US011992364B2

(12) United States Patent
Fatemi et al.

(10) Patent No.: US 11,992,364 B2
(45) Date of Patent: May 28, 2024

(54) LOSS-ANGLE-BASED DETERMINATION OF A MEDIUM VISCOELASTIC PARAMETER IN SUB-HERTZ FREQUENCY RANGE WITH THE USE OF LOCAL CREEP RESPONSE

(71) Applicant: Mayo Foundation for Medical Education and Research, Rochester, MN (US)

(72) Inventors: Mostafa Fatemi, Rochester, MN (US); Alireza Nabavizadehrafsanjani, New York, NY (US); Azra Alizad, Rochester, MN (US); Mahdi Bayat, Rochester, MN (US)

( * ) Notice: Subject to any disclaimer, the term of this patent is extended or adjusted under 35 U.S.C. 154(b) by 607 days.

(21) Appl. No.: 16/324,776

(22) PCT Filed: Aug. 10, 2017

(86) PCT No.: PCT/US2017/046222
§ 371 (c)(1),
(2) Date: Feb. 11, 2019

(87) PCT Pub. No.: WO2018/031725
PCT Pub. Date: Feb. 15, 2018

(65) Prior Publication Data
US 2019/0175140 A1 Jun. 13, 2019

Related U.S. Application Data

(60) Provisional application No. 62/373,926, filed on Aug. 11, 2016.

(51) Int. Cl.
*A61B 8/08* (2006.01)
*A61B 8/00* (2006.01)

(52) U.S. Cl.
CPC .............. *A61B 8/085* (2013.01); *A61B 8/403* (2013.01); *A61B 8/4209* (2013.01); *A61B 8/463* (2013.01);
(Continued)

(58) Field of Classification Search
CPC ....... A61B 8/085; A61B 8/403; A61B 8/0825; A61B 8/54; A61B 8/5207; A61B 8/5223;
(Continued)

(56) References Cited

U.S. PATENT DOCUMENTS 8,137,275 B2   3/2012  Fan et al.
8,734,351 B2 * 5/2014  Waki ...................... A61B 8/463
                                               600/442

(Continued)

FOREIGN PATENT DOCUMENTS

JP     2004267464 A  *  9/2004

OTHER PUBLICATIONS

Sridhar, Mallika, and Michael F. Insana. "Ultrasonic measurements of breast viscoelasticity." Medical physics 34.12 (2007): 4757-4767. (Year: 2007).*

(Continued)

*Primary Examiner* — Joel Lamprecht
*Assistant Examiner* — Brooke Lyn Klein
(74) *Attorney, Agent, or Firm* — Quarles & Brady LLP

(57) ABSTRACT

System and method configured to characterize viscoelasticity of a target medium by directly determining phase difference between real and imaginary parts of the complex shear modulus of the tissue (determined as a result of applying a compression force to the tissue), without any fitting of data and independent from distribution of strain in the tissue caused by the application of compression force.

17 Claims, 15 Drawing Sheets

(52) U.S. Cl.
CPC .............. *A61B 8/483* (2013.01); *A61B 8/485* (2013.01); *A61B 8/5207* (2013.01); *A61B 8/5223* (2013.01); *A61B 8/5246* (2013.01); *A61B 8/5276* (2013.01); *A61B 8/54* (2013.01); *A61B 8/587* (2013.01)

(58) Field of Classification Search
CPC ....... A61B 8/4209; A61B 8/463; A61B 8/483; A61B 8/5246; A61B 8/5276; A61B 8/587; A61B 8/485; G16H 50/30
See application file for complete search history.

(56) References Cited

U.S. PATENT DOCUMENTS

| | | | |
|---|---|---|---|
| 8,753,278 B2 | 6/2014 | Stoll | |
| 2009/0177083 A1* | 7/2009 | Matsumura | B06B 1/067 600/437 |
| 2012/0108968 A1 | 5/2012 | Freiburger et al. | |
| 2014/0206995 A1* | 7/2014 | Oikawa | A61B 8/403 600/438 |
| 2014/0221833 A1* | 8/2014 | Nagae | A61B 8/0858 600/438 |
| 2014/0288424 A1* | 9/2014 | Mukdadi | A61B 8/483 600/438 |
| 2015/0126866 A1 | 5/2015 | Miyake | |
| 2015/0150535 A1 | 6/2015 | Fan et al. | |
| 2016/0135788 A1* | 5/2016 | Greenleaf | G01S 7/52042 600/438 |
| 2016/0143624 A1* | 5/2016 | Liberman | A61B 8/5207 600/431 |
| 2017/0145202 A1* | 5/2017 | Sparks | B29B 7/7457 |

OTHER PUBLICATIONS

Amador, Carolina, et al. "Loading ramp effects in uniaxial compression creep device." 2014 IEEE International Ultrasonics Symposium. IEEE, 2014. (Year: 2014).*

International Search Report and Written Opinion dated Oct. 19, 2017 from Parent Application PCT/US17/46222, 17 pages.

* cited by examiner

FIG. 15A
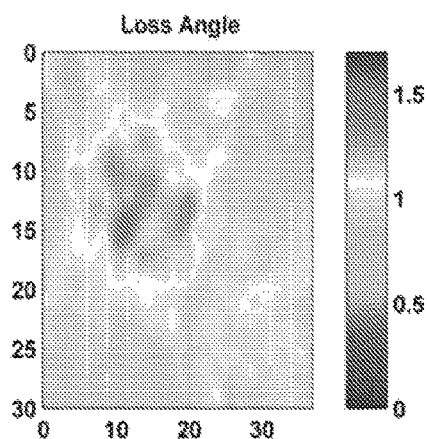
FIG. 15B
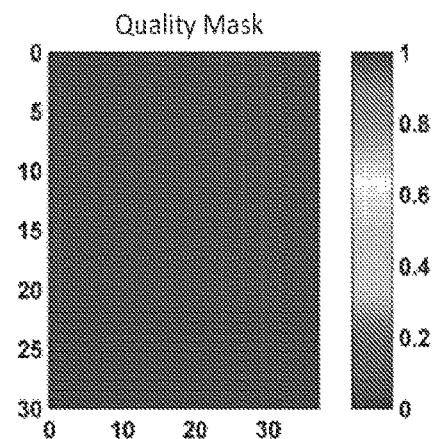
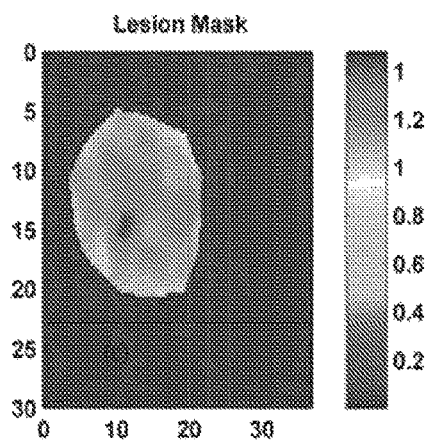
FIG. 15C
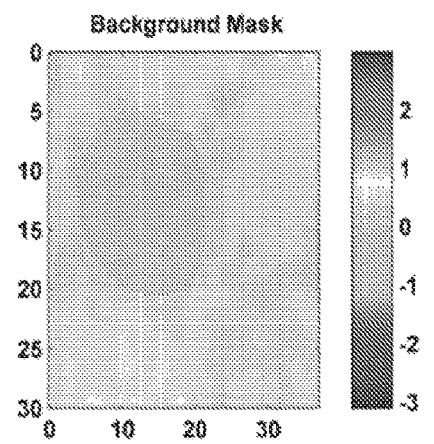
FIG. 15D
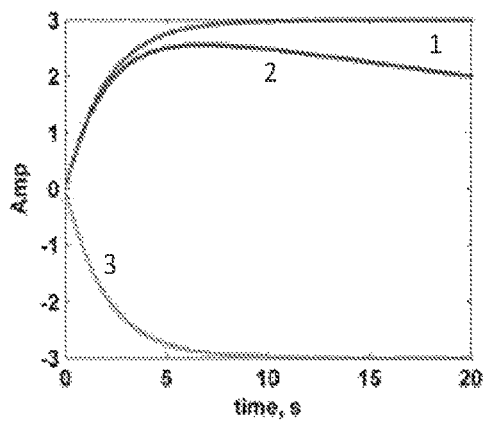
FIG. 16A
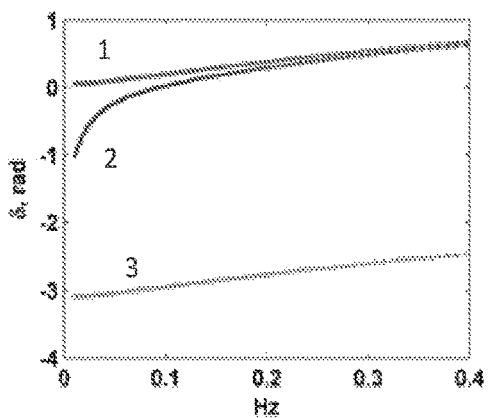
FIG. 16B
1 ——— Ev,T1=2
2 ——— Ev,T1=2, Negative slope
3 ——— Ev,T1=2, Negative strain FIG. 20A
FIG. 20B
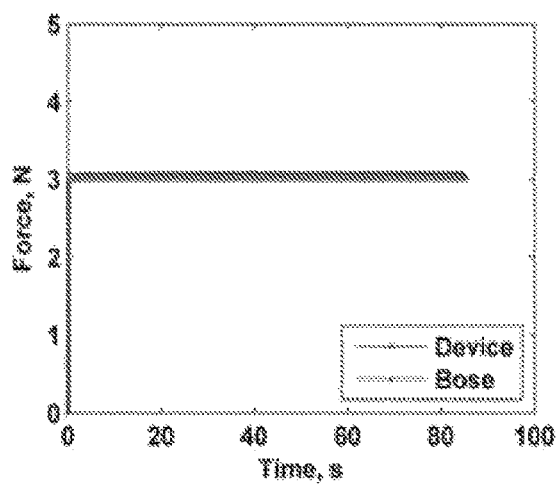
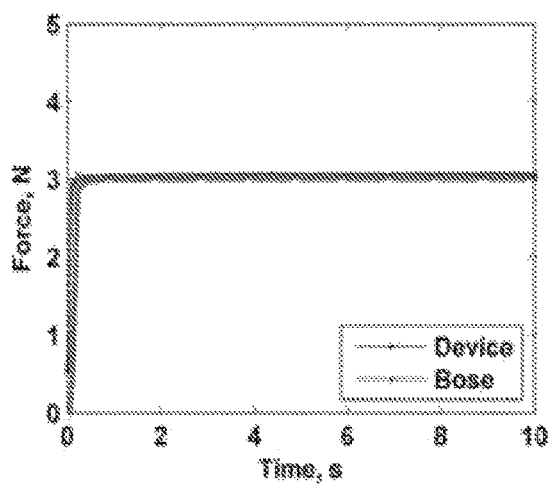
FIG. 21A
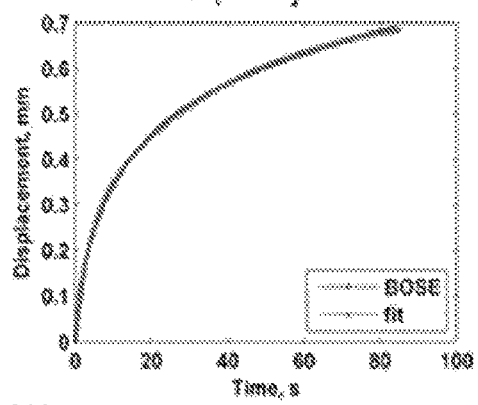
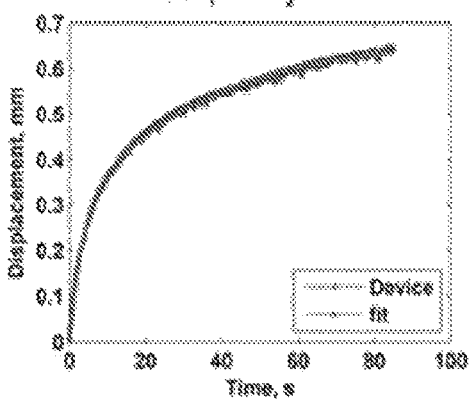
FIG. 21B
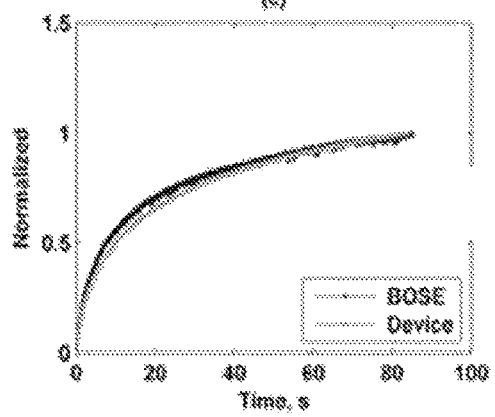
FIG. 21C

LOSS-ANGLE-BASED DETERMINATION OF A MEDIUM VISCOELASTIC PARAMETER IN SUB-HERTZ FREQUENCY RANGE WITH THE USE OF LOCAL CREEP RESPONSE

CROSS-REFERENCE TO RELATED APPLICATIONS

This patent application is a U.S. 371 national phase entry application of International Application No. PCT/US2017/046222, filed Aug. 10, 2017, which claims priority from U.S. Provisional Application No. 62/373,926, filed on Aug. 11, 2016 and titled "System and Methods for Imaging Tissue Viscoelastic Properties in Frequency Domain". The disclosures of each are incorporated herein by reference as if set forth in their entireties for all purposes.

STATEMENT REGARDING FEDERALLY SPONSORED RESEARCH AND DEVELOPMENT

This invention was made with government support under CA168575 awarded by the National Institutes of Health. The government has certain rights in the invention.

BACKGROUND

Viscoelastic mechanical properties of tissue can be assessed, intrinsically and noninvasively, with the use of the so-called ultrasonic creep test. This methodology includes the ultrasonic application of a step-force to the tissue and ultrasonic monitoring of the local viscoelastic strain response to such force. While so applied, the step-force is used as a stimulus, and the transient strain/stress response (which is governed by viscoelastic properties of the medium) is monitored by recording a sequence of radiofrequency (RF) data (image frames, for example) during the excitation of acoustic radiation force with the applied to the tissue front of ultrasound.

The ultrasonic creep test has two recognized varieties: an internal test and an external test (differentiated based on the type of excitation). In the internal ultrasonic creep test, the acoustic radiation force is employed to apply a step force, inside the medium and to a local portion of it, without any changes in boundary condition, geometry, or shape while exciting the medium. In the external ultrasonic creep test, a quasi-static stimulus is applied to the entire, overall medium by an ultrasound probe. In this case, the probe motion is driven either manually or automatically for a predetermined time with no contribution of acoustic radiation force. The external ultrasound creep test is more commonly used, and can be considered to be the basis for a specific elastography method used for a study of the viscoelastic properties of the medium—rather than the elasticity of the medium.

In order to quantify the viscoelastic creep behavior of the medium in time domain, related art utilizes a process of fitting the multi-exponential creep curves (representing the corresponding experimental data) to a low-order discrete Voigt model (to estimate the retardation times. It is also possible to assess the viscoelastic properties of time-dependent creep response in frequency domain. Here, for example, R. Evans et al. (*Physical Review Letts.*, vol. 80, p. 012501, 2009), devised a formula that converts time-domain creep compliance to frequency-domain complex modulus in a model-independent way. The same method was later used to quantify viscoelastic properties by estimating the complex elastic modulus and loss tangent from time-dependent creep responses induced by acoustic radiation force.

The problem with assessment of the viscoelastic parameter based on the fitting of data curves (on which the related art has relied up to-date) is that of accuracy and precision. Indeed, the fitting-based evaluation does not rely on actual, real, acquired data (but instead on the data arrived at by approximating the real data with a fitting curve) and, therefore, inherently contains an error caused by the data-fitting process. There remains a need in methodology for evaluation of the viscoelastic properties of the medium that correct this shortcoming.

SUMMARY

Embodiments of the invention provide a system for ultrasound imaging of a compressed target object. Such system includes a compression device configured to apply a force to the target object while varying the amount of force at a constant rate from an initial amount to the final predetermined amount, and, once the final predetermined amount is reached, maintaining the applied force to keep a substantially constant level of pressure on the tissue. The system also includes an ultrasound probe containing an ultrasound transducer. The probe is mechanically associated with the compression device and configured to receive an ultrasound wave from the target object during a duration of time while the compression device holds the ultrasound probe in contact with the target object and while the force is being applied to the target object. The system further includes an ultrasound imaging system cooperated with the ultrasound probe and configured to record a sequence of ultrasound image data frames during the duration of time. The ultrasound image data frames represent a region of interest (ROI) of said target object. Additionally, the system includes a compression device controller, operably cooperated with the compression device and including electronic circuitry programmed to set and control the constant rate at which the force is applied and to synchronize an operation of the compression device with an operation of the ultrasound imaging system. The system also includes a data-processing unit configured to receive signal outputs produced at least by the ultrasound imaging system and the compression device controller to determine, based on the signal outputs, a value of local stress of the target object at each target object point that has been imaged, with the ultrasound imaging probe, as a function of time.

In a specific case, the system is configured to determine a value of loss angle parameter as a ratio of imaginary and real parts of a complex shear modulus of the target object that has been assessed independently from a distribution of the local stress in the target object, where the distribution of the local stress has been caused by the force applied to the target object with the use of the compression device. Alternatively or in addition, the data-processing unit is configured to determine the loss angle parameter in a range of frequencies defined to allow a determination of viscoelasticity of the target object as a function of at least one of frequency and time.

In one embodiment, the data-processing unit is further configured to perform at least one of the following: (i) to identify, based on the sequence of image frames and a signal output from the ultrasound imaging system, a target object location at which a time-dependence of the value of local stress does not follow a behavior of local stress expected in a viscoelastic medium, by (a) identifying a sign of a slope of said time-dependence, and (b) assigning a marker of unreliability to a portion of acquired data corresponding to a portion of the curve that has a negative sign; (ii) to form a map of loss angle parameter across an imaged portion of the target object and generate a data mask configured to eliminate data points associate with the marker of unreliability from said map; and (iii) to filter out, from the signal outputs produced at least by the ultrasound imaging system and the compression device controller, an interference signal caused by presence of at least one of a cardiac pulsation, breathing motion, residual effect of initial ramping of the compression device, and noise, by processing the signal outputs within a frequency range that is devoid of such interference signal. Alternatively or in addition, the data-processing unit may be configured to determine a value of loss angle parameter based on determining a complex shear modulus of the target object in a sub-Hertz frequency range.

In a related embodiment, the ultrasound imaging system is configured to effectuate at least one of the following: (i) to display a map of the loss angle parameter as a color overlay over an image of the target object procured in B-mode of operation of the ultrasound probe; (ii) to record the sequence of the image frames, each image frame representing a 2D image of the target object; (iii) to record the sequence of the image frames each representing a 3D image of the target object and generate a signal output further used by the data-processing unit to determine the loss angle in 3D space; and (iv) to record the sequence of the image frames at a rate of hundreds of frames per second while the target object is insonated with an ultrasound wave shaped as either a substantially plane wave or a spatially-localized beam, wherein a shape of the ultrasound wave is chosen depending on a compression rate of the target object.

Furthermore, in a specific case the data-processing unit may be programmed to perform at least one of the following (i) to calculate a complex shear modulus at each ultrasonically-imaged point of the target object in frequency domain by directly converting values of local stress into Fourier domain; and (ii) to calculate a complex shear modulus at each ultrasonically-imaged point of the target object from a profile of values of the local stress in time domain; and, once the complex shear modulus has been determined, calculate a loss angle parameter based on a ratio of imaginary and real parts of the complex shear modulus and form a map of such loss angle parameter across an imaged portion of the target object. In this specific case, the system may be further configured to accept a marking of a lesion area in an ultrasound image frame acquired with the ultrasound imaging system (such marking provided as an external input to the data-processing unit); to transfer this marking to the map of the loss angle parameter to identify the lesion area on the map; and to determine a first average value of the loss angle parameter within the lesion area of the map and a second average value of the loss angle parameter in a remaining portion of the map while not accounting for data at such points on the map at which a slope of time-dependence of said value of local stress has a negative sign.

Embodiments of the invention also provide a method for ultrasound imaging of a compressed target object. An embodiment of the method includes:

with an automated compression device, applying force to the target object while varying such force from an initial value to the final predetermined value and, once the final predetermined value is reached, maintaining such force at a substantially constant level;

receiving an ultrasound wave from the target object, insonated with an ultrasound transducer of the ultrasound probe during a period of time while the target object is compressed with the applied force;

with an ultrasound imaging system, recording a sequence of ultrasound image data frames during the period, based on data from said ultrasound wave (the ultrasound image data frames representing a region of interest, ROI, of the target object; and with a programmable computer processor, operably cooperated with at least the compression device and the ultrasound imaging system, determining a value of local stress at each the target object point, that has been insonated with said ultrasound transducer, as a function of time.

In one embodiment, the method may additionally include a step of assessing a value of loss angle parameter as a ratio of imaginary and real parts of a complex shear modulus of the target object that has been determined based on said data and independently from a distribution of the local stress in the target object; and/or a step of assessing the loss angle parameter in a range of frequencies defined to allow a determination of viscoelasticity of the target object as a function of at least one of frequency and time. An embodiment of the method may addition include one of more of the following steps:

(i) identifying, based on the sequence of image frames and a signal output from the ultrasound imaging system, a target object location at which a time-dependence of the value of local stress does not correspond to that in a viscoelastic medium, by (a) identifying a sign of a slope of said time-dependence, and (b) assigning a marker of unreliability to a portion of acquired data corresponding to a portion of the curve that has a negative sign;

(ii) forming a map of loss angle parameter across an ultrasonically imaged portion of the target object and generating a data mask configured to eliminate data points associated with the marker of unreliability from said map;

(iii) filtering out, from the signal outputs produced at least by the ultrasound imaging system and a controller of the compression device, an interference signal caused by presence of at least one of a cardiac pulsation, breathing motion, residual effect of initial ramping of the compression device, and noise, by processing the signal outputs within a frequency range that is devoid of such interference signal.

In such embodiment, the method may further include a step of assessing a value of loss angle parameter based on the measurements of a complex shear modulus of the target object in a sub-Hertz frequency range.

In a related embodiment, the method additionally includes at least one of the following: (i) displaying a map of the loss angle parameter as a color overlay over an image of the target object procured in B-mode of operation of the system; (ii) recording the sequence of the image frames, each image frame representing a 2D image of the target object; (iii) recording the sequence of the image frames each representing a 3D image of the target object and generating a signal output further used by a data-processing unit of the ultrasound imaging system to determine the loss angle in 3D space; and (iv) recording the sequence of the image frames at a rate of hundreds of frames per second while the target object is insonated with an ultrasound wave shaped as either a substantially plane wave or a spatially-localized beam, wherein a shape of the ultrasound wave is chosen depending on a compression rate of the target object with said force.

Alternatively or in addition, the method comprises at least one of the following
(i) calculating a complex shear modulus at each ultrasonically-imaged point of the target object in frequency domain by directly converting values of local stress into Fourier domain; and
(ii) calculating a complex shear modulus at each ultrasonically-imaged point of the target object from a profile of values of the local stress in time domain;
and further comprises:
once the complex shear modulus has been determined, calculating a loss angle parameter based on a ratio of imaginary and real parts of the complex shear modulus and forming a map of said loss angle parameter across an imaged portion of the target object. In a specific implementation, such method may additionally incorporate:
marking a lesion area in an ultrasound image frame, acquired with the ultrasound imaging system, said marking provided as an external input to the data-processing unit of the system;
transferring such marking to the map of the loss angle parameter to identify the lesion area on the map;
and
determining a first average value of the loss angle parameter within the lesion area of the map and a second average value of the loss angle parameter in a remaining portion of the map while not accounting for data at such points on the map at which a slope of time-dependence of said value of local stress has a negative sign.

BRIEF DESCRIPTION OF THE DRAWINGS

FIG. 2A: one exponential input with and without heartbeat. FIG. 2B: δ profile in frequency range below 2 Hz.

FIG. 5A contains the $T_1$ map. FIG. 5B presents the error fit map. FIG. 5C shows strain behavior (curve 510) of the point 1 of FIG. 5A and its Kelvin-Voigt fit, (curve 520) with its $T_1$ value. FIG. 5D demonstrates the behavior of the loss angle resulting from applying the Evans method to strain profile 510 of the point 1, and applying the Evans method to the fit curve (curve 520) of the strain profile, and applying the analytical method to the curve 520 (curve 530).

FIG. 6A: the loss angle, δ, map obtained by applying Kelvin-Voigt methods to a fitted curve of the strain profile, Analytical method. FIG. 6B: the δ map based on applying Evans methods to the strain profile.

FIG. 6D: a δ map at 0.16 Hz; FIG. 6E: a δ map produced at 0.19 Hz; FIG. 6F: a δ map produced at 0.23 Hz; FIG. 6G: a δ map produced at 0.26 Hz.

FIG. 7A: T1 map of stiff uniform phantom with cutting point of 1 second. FIG. 7B: T1 map of stiff uniform phantom with cutting point of 3 seconds.

Maps for loss angles obtained at 0.17 Hz, for different cutting point in stiff and soft uniform phantoms, corresponding to FIGS. 7A through 7D.

FIG. 9A: T1 map with a cutting point of 1 second. FIG. 9B: T1 map with a cutting point of 3 seconds.

The loss angle maps created at 0.17 Hz, for different cutting points in an inclusion phantom.

FIGS. 15A, 15B, 15C, 15D provide illustrations for an inclusion phantom. FIG. 15A: loss angle map. FIG. 15B: Quality mask. FIG. 15: lesion mask for measuring loss angle of inclusion part. FIG. 15D: background mask for measuring the loss angle of background part.

FIG. 16A: Strain profiles; FIG. 16B: Loss angle profiles corresponding to FIGS. 15A through 15D.

FIGS. 20A, 20B illustrates the operational comparison of the conventional Bose instrument and the compression device configured according to an embodiment of the invention to generate 3 N force with 18 N/s ramp. The ramp part takes 0.17 seconds and after that the force remains constant for 85 seconds. FIG. 20A: Force profile for the entire 85 sec. FIG. 20B Force profile for 10 seconds presented for better visualization.

FIGS. 21A, 21B, 21C: Surface displacement profiles assessed with the use of embodiments of FIGS. 17 and 19. FIG. 21A: Bose (embodiment 1900) displacement profile and its fit with $T_1$ and $T_2$ value results. FIG. 21B: Compression device (embodiment 1700) displacement profile and its fit with $T_1$ and $T_2$ value results. FIG. 21C: normalized displacement profiles for embodiments 1700, 1900.

DETAILED DESCRIPTION

Figure 1A:
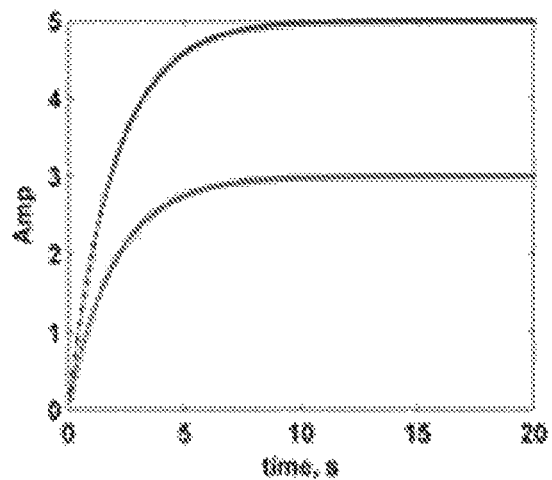
FIGS. 1A, 1B, 1C, and 1D present plots illustrating the effects of the amplitude (A) and the $T_1$ values on the value of the loss angle in the low-frequency range (below 0.4 Hz).

As was already alluded to above, evaluation of the viscoelastic property of the medium based on curve-fitting of data acquired with the creep test (a standard used in related art) is not accurate and, therefore, not reliable. The problem of lack of accuracy and/or precision of the determination of the viscoelastic property(ies) of the target medium is solved by embodiments of the present invention. The accuracy and/or precision of such determination are increased by assessing the local viscoelastic properties of the medium via direct use and analysis of the temporal strain response of the creep test in the frequency domain. With the use of the proposed solution, the ratio of the dissipated energy to the stored energy (or, the ratio of the loss modulus to the storage modulus) is determined. In particular, according to the idea of the invention, the phase difference δ between the storage and loss moduli (also referred to as loss angle), resulting from the analysis of the local strain response of the creep test carried out in the sub-Hertz frequency range, is utilized for evaluation of the sought-after viscoelastic properties.

The term "loss tangent" is used to define the ratio of the imaginary component of the complex modulus to the real component of the modulus. The imaginary part of the complex modulus is referred to as the "loss modulus", while the real part of the complex modulus is referred to as the "storage modulus". The loss modulus indicates the dissipation of energy in the medium, whereas the storage modulus represents the energy stored in the system during the application of force or stress. Accordingly, the storage modulus defines the elastic deformations under stress, while loss modulus describes the viscous deformation.

The medium characterized by the smaller loss tangent is recognized to be more elastic than the medium that absorbs energy through viscous processes and that has a higher loss tangent (see M. Ueshige et al., in *Journal of Dentistry*, vol. 27, pp. 517-522, 1999). Consequently, evaluation of the viscoelastic response of the medium in the spectral domain can be carried out with the assessment of the loss tangent.

Measuring either the complex compliance, or storage and loss parameters (or their ratio as a loss tangent) is commonly carried out with a standard mechanical device. Generally, such a standard mechanical device is configured to apply an oscillating stress at different frequencies to the target medium, while the strain response at each of the frequencies is detected. By measuring the phase difference between the stress (as stimulus) and strain (as the response), it is possible to quantify the loss tangent at different frequencies (for example, in a specific frequency range). Although such standard mechanical device can be employed to measure the loss tangent very accurately, it remained impractical (or even impossible) to use a mechanical device for an in vivo study and for measuring the loss tangent locally in the medium. Indeed, for any of conventionally-used to-date mechanical devices the sample size and the geometry are important factors, and, as a result, the measurement is mostly aimed at measuring the surface displacement or surface strain of the sample—not the displacement or strain inside the sample. This is the reason that all the studies that have been done so far focused on a sample of tissue and worked in vitro.

Several studies either directly or indirectly confirm that the viscous contribution to viscoelastic response at lower frequency range is greater than (or superior to) that at the higher frequency range, especially when it comes to the spectrum of the creep response, covering a wide range of frequencies depending on a) the initial rising part of temporal creep response, which relates to high frequency components; and b) the whole duration of the creep response, which corresponds to the low frequency components of the spectrum.

The above-described situation begs a question of whether the analysis of the low-frequency components of the creep spectra are particularly beneficial for the determination of viscoelastic properties of the target medium. As discussed below, this question was addressed by studying the effect of viscous component(s) on contrast of the determined characteristic in a low-frequency range, as frequencies below about 0.4 Hz. In addition, in this range of frequencies the spectrum is not as noisy as that at higher frequencies. Furthermore, the effect of the ramp part of the force stimulus in external ultrasonic creep test on the spectral creep estimation at low frequencies is minimal. The fully-automated compression system, employed for conducting the required measurements and assisting with differentiation between the malignant and benign formations in the tissue based on the determination of the viscoelastic properties is also disclosed (Appendix A).

The validation of the idea of the invention was carried out by, first, computing the phase difference between the storage and loss moduli with the use of the Evans method to the local time-dependent creep response. Additionally, the method was validated with a standard model (such as Kelvin-Voigt) as it relates to measuring δ in the low-frequency range.

1. Examples of Methodologies 1.1 Retardation Time and Measurement of δ

It is recognized in related art that the response of the viscoelastic material to stress is related to both the strain and strain rate. The Kelvin-Voigt model, expressed in Eq. (1), represents such behavior as $$\sigma(t) = E\varepsilon(t) + \eta \frac{d\varepsilon(t)}{dt}, \tag{1}$$

where E is the material's elasticity and η is the viscosity parameter. When suddenly applying constant stress $\sigma_0$ to the medium, the response of a Kelvin-Voigt material can be described as $$\varepsilon(t) = \frac{\sigma_0}{E}\left(1 - \exp\left(\frac{-t}{T_1}\right)\right). \tag{2}$$

In Eq. (2), the retardation $T_1$ is defined as $$T_1 = \frac{\eta}{E}, \quad (3)$$

and its value is related to the viscosity and elasticity of the viscoelastic medium (see, for example, C. Amador et al., in Physics in Medicine and Biology, vol. 57, p. 1263, 2012; incorporated herein by reference).

Applying the Laplace transform to Eq. (2) makes it possible to extract storage and loss moduli in the spectral domain which are called storage and loss moduli. The complex dynamic modulus of a Kelvin-Voigt material is given by:

$$E^* = E + i\eta\omega \quad (4)$$

The magnitude, M, of the complex dynamic modulus can be defined as:

$$M = \sqrt{E^2 + (\eta\omega)^2} \quad (5)$$

The ratio between the imaginary and real parts of the complex dynamic modulus is the loss tangent, calculated as $$\tan(\delta) = \eta\omega/E \quad (6).$$

Accordingly, the phase difference $\delta$ is determined as $$\delta = \arctan(\eta\omega/E) \quad (7)$$

1.2 Evans' Method and Measurement of $\delta$; Model Free Methods.

The determination of a loss tangent can assist in evaluating the viscoelastic response of the medium. According to the idea of the invention, the assessment of the loss tangent is carried out by considering the local creep response of the medium and the use of Evans' method. The following Eq. 8 can be used to convert the time-dependent compliance, J(t), to complex shear modulus, $G(\omega)$:

$$G^*(\omega) = \frac{i\omega}{i\omega J(0) + \exp[-i\omega t(N)]/\eta + \sum_{n=1}^{N}\left\{\frac{J(n) - J(n-1)}{t(n) - t(n-1)}\right\}(\exp(-i\omega t(n-1)) - \exp(-i\omega t(n)))} \quad (8)$$

where n is time sample index, J(0) is the compliance at n=0 (which is estimated by extrapolation of the compliance function to t→0. The parameter $\eta$ represents the steady-state viscosity, which is estimated by extrapolation of compliance function to t→∞. The unique characteristic of this equation is its independence from fitting the theoretical model to convert time-dependent compliance, J(t), to the complex shear modulus, $G^*(\omega)$ $$\tan(\delta) = G_i(\omega)/G_s(\omega) \quad (9),$$

where $G_i(\omega)$ and $G_s(\omega)$ are the imaginary and real parts, respectively, of the complex shear modulus presented by Eq. (8).

Thus, the value of the loss angle $\delta$ is equal to $$\delta = \arctan(G_i(\omega)/G_s(\omega)) \quad (10).$$

One of the important aspects of measuring loss tangent and loss angle, $\delta$ (with either internal or external ultrasonic creep test) is that despite the storage modulus and the loss modulus, the loss angle and the loss tangent are independent of the stress distribution in the medium.

2. Examples of Types of Simulation 2.1 Validation of Loss Angle Method Based on Kevin-Voight Model In order to assess the performance of the Evans' method, we performed the simulation based on one exponential creep response. Eq. (2) and compared the results expressing the loss angle $\delta$ for both the analytical methods, Eq. (7), and the Evans' method, Eq. (10).

The time-dependent creep response was simulated as an exponential Kelvin-Voigt model, with Eq. (2) providing input for all the simulation cases. In this equation, the amplitude is the ratio of the stress to strain, $\sigma_0/E$, and for all the simulation cases it is assumed that $\sigma_0=1$ pa. In the following Figures the analytical part is denoted as Ana, and is compared with Evans' method denoted as Ev.

Figure 1B:
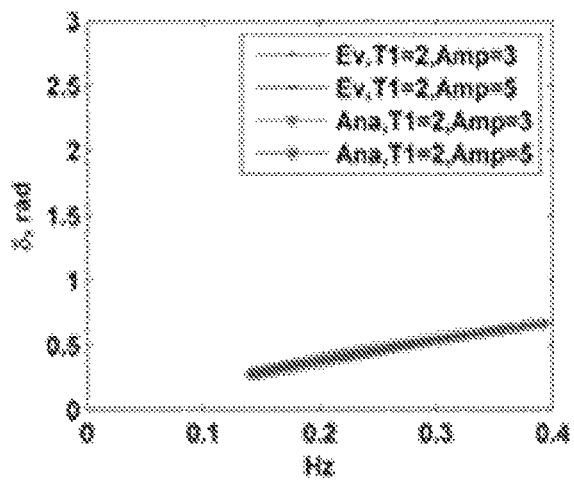
Figure 1C:
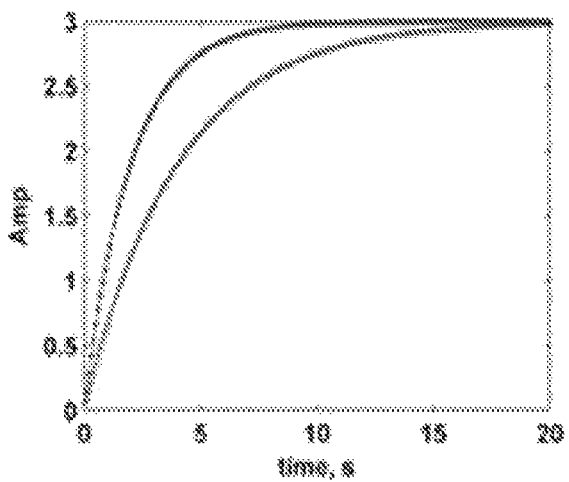
Figure 1D:
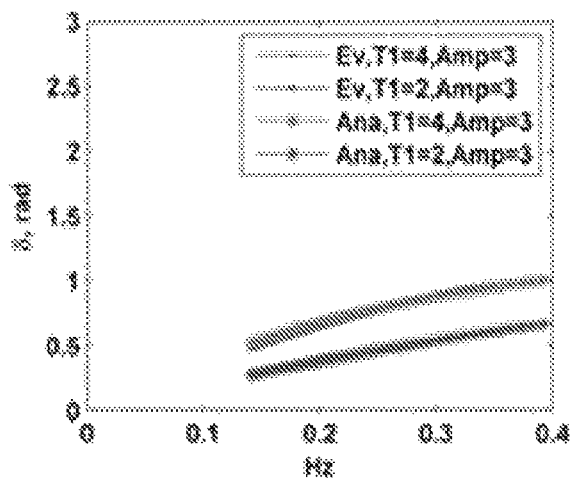

Specifically, FIGS. 1A, 1B, 1C, and 1D illustrate noise-free cases, and present the behavior of the loss angle $\delta$ due to difference in amplitude, A, and $T_1$ values for Eq. (2) as an input. Here, FIG. 1A illustrates inputs with the same $T_1$ values but different amplitudes; FIG. 1B: $\delta$-profiles corresponding to FIG. 1A. It can be seen that both of $\delta$-profiles—the one resulting from the analytical method and the one resulting from the Evans' method—are in agreement and the variation in amplitude does not affect the $\delta$ profile. In case of FIG. 1C, inputs are presented with the same amplitudes A but different $T_1$ values, and FIG. 1D provides $\delta$-profiles corresponding to the inputs of FIG. 1C. Again, the $\delta$ profiles resulting from the application of both methods have the same trend in this range of frequencies, but the model with higher $T_1$ value has higher $\delta$ values as compared with the model having the lower $T_1$ value.

2.2 Heart Beat Simulation

When it comes to exposing a breast tissue of a patient to the creep test, there are always two sources of motions present that can have a negative influence on recorded data or resulting images: respiration and cardiac motion. While the patient can be asked to stop breathing for a certain period of time, to improve the quality of recorded data, heart beat always affects local creep response of the breast tissue.

Figure 2A:
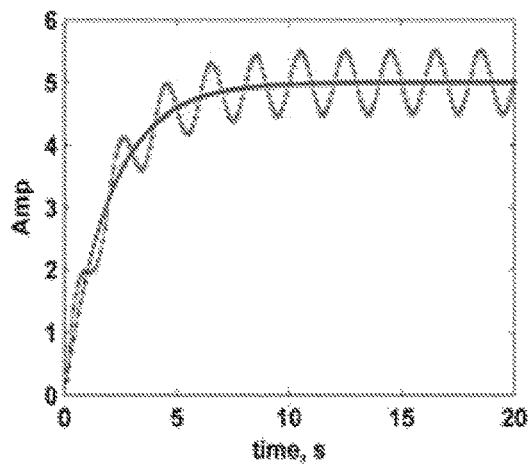
FIGS. 2A and 2B illustrate the effect of the heart beat on the loss angle in the frequency range less than 2 Hz.
Figure 2B:
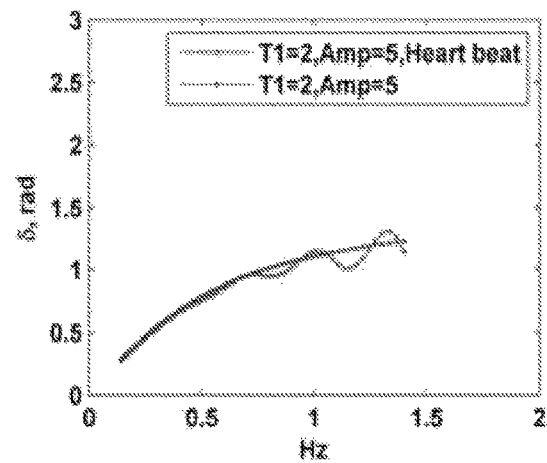

Accordingly, the effect of the heart beat on the creep response was simulated. To this end, a single exponential curve representing the input according to Eq. (2) was complemented with a 1 Hz sinusoidal curve representing the heart-beat. FIGS. 2A, 2B illustrate the results.

As can be observed from FIG. 2B, the motion of the tissue caused by the heartbeat does not affect the profile of the loss angle significantly in the frequency range below 0.4 Hz. This simulation evidences yet another advantage of using the $\delta$ profile for the analysis of the creep response in in vivo study (for example, in the in vivo study of the breast tissue). Notably, an interference signal caused by presence of at least one of a cardiac pulsation, breathing motion, residual effect of initial ramping of the compression device, and auxiliary noise, can be eliminated from the collection and/or processing of data according to an embodiment of the invention by processing acquired ultrasonic data within a frequency range that is devoid of such interference signal.

3. Phantom Studies 3.1 Phantom Recipe

The phantom study of the idea of the invention was carried out by forming two uniform cubic phantoms (one stiff and the other soft), and creating a third inclusion phantom, in which the background material was similar to that of the soft cubic phantom, and the cylindrical inclusion was made from the same material as that of the stiff cubic phantom.

The cubic phantom dimensions were 7.5 cm×5.5 cm×2 cm (L×W×H) for both phantoms. The inclusion phantom dimensions are 7.5 cm×5.5 cm×5.5 cm (L×W×H), with the cylindrical inclusion having a 1.5 cm diameter. The stiff phantom was made of 25.14 grams of gelatin (Sigma-Aldrich; St. Louis, MO); 60 ml propylene glycol (Sigma-Aldrich, St. Louis, MO); and 4 grams cellulose (Sigma-Aldrich) for ultrasound scattering, dissolved in enough distilled water to make the total solution volume equal 300 ml. For the soft phantom, we used 32.3 grains gelatin (Sigma-Aldrich, St. Louis, MO); 30 ml Vanicream Lite (Pharmaceutical Specialties, Inc., Rochester, MN); 6 grams cellulose (Sigma-Aldrich) for ultrasound scattering; and 6 grams potassium sorbate (Sigma-Aldrich) as a preservative, dissolved in enough distilled water to make the total solution volume equal 600 ml.

After preparing these phantoms, the retardation time, $T_1$ was assessed by using curve-fitting method. Later, by applying the model-free methods, the loss angle maps based on the same data were demonstrated.

3.2 Mapping the Retardation Time, T1

An automated compression device, described in the U.S. Provisional Application No. 62/373,926, the disclosure of which is incorporated herein by reference in its entirety, was used to apply an approximate step force on a medium of choice to measure the retardation time $T_1$.

A short summary of the compression device is presented in Appendix A.

Such compression device was used in this study to apply an 8 N force with 16 N/s ramp on each of the aforementioned phantoms. Then, to monitor the phantom response, a Verasonics ultrasound system (Verasonics, Inc., Kirkland, WA, USA) with a linear array transducer (L11-4v, Verasonics, Inc., Kirkland, WA, USA) was used. Plane wave imaging mode of this system was employed to acquire a series of B-mode images of the phantom during compression. The ultrasound center frequency was 6.43 MHz. The frame rate was 20 Hz during the acquisition time of 20 seconds; thus 400 frames were acquired for each of the phantom experiments.

The initial two seconds of data were ignored to ensure that the force reached the steady state and that the viscoelastic portion of the creep response was entered.

Figure 3A:
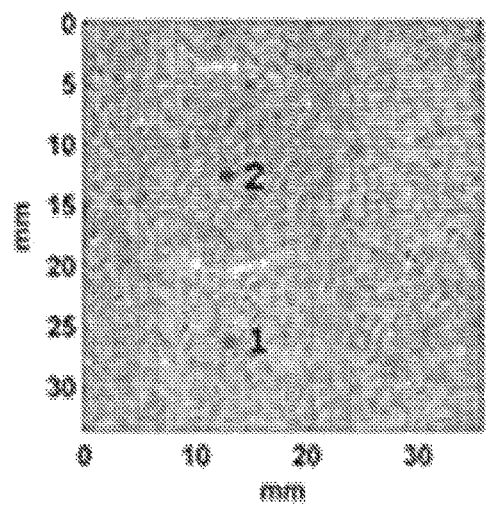
FIG. 3A illustrates the ultrasound B-mode image of inclusion phantom.
Figure 3B:
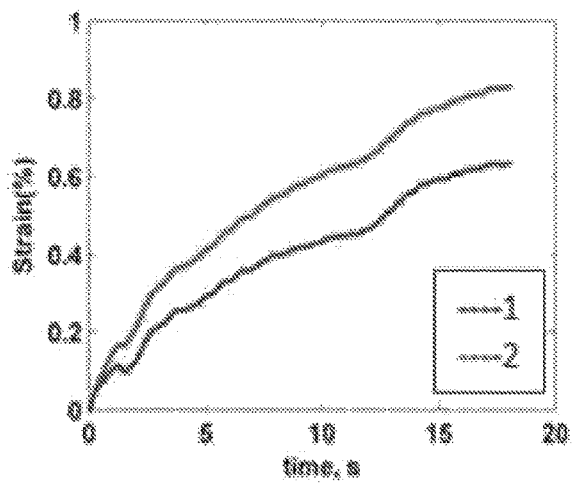
FIG. 3B demonstrates the strain profile of points specified in FIG. 3A.

The ultrasound B-mode image of the inclusion phantom and the strain behavior of two specified points are illustrated in FIGS. 3A and 3B. In order to reduce memory needs and processing time for the inclusion phantom, only an axial portion (approximately 3.5 cm of B-mode images in the axial direction) were considered; and for uniform cubic phantoms, only a 1.8 cm portion of B-mode images were considered. All of these experiments were done at room temperature.

Figure 4A:
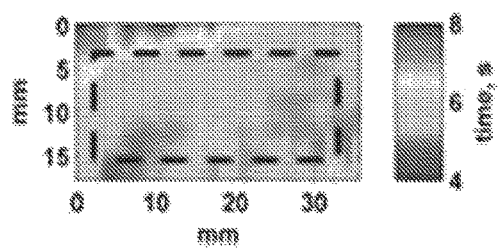
FIGS. 4A, 4B, and 4C illustrate the resultant $T_1$ maps of three identified phantoms.
Figure 4B:
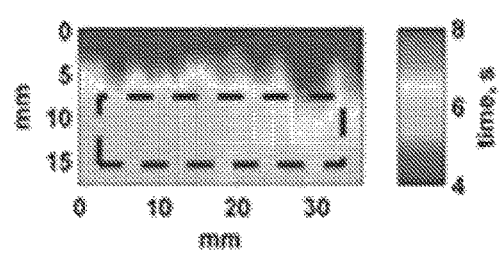
Figure 4C:
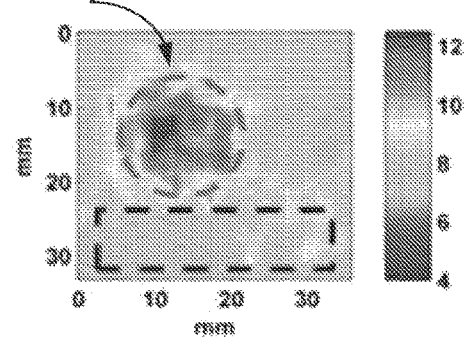

FIGS. 4A, 4B, and 4C illustrate $T_1$ maps for a cubic soft phantom (FIG. 4A); a cubic stiff phantom (FIG. 4B); and a phantom inclusion (FIG. 4C). The black dashed rectangles represents the area that has been considered for measuring $T_1$ values. In phantom inclusion (FIG. 4C) the red circle 410 shows the area to measure $T_1$ value for inclusion. The $T_1$ value for these phantoms have been measured based on the average value of black dashed rectangle in cubic soft and stiff phantoms. For cubic soft phantom the calculated $T_1$ value was 7 seconds, and for soft cubic phantom $T_1$ value was 5.8 seconds. For inclusion phantom the average $T_1$ value for inclusion part was 9 seconds and for the background part of this phantom was around 7.5 seconds.

3.3 Mapping the Loss Angle, δ

3.3.1 Loss Angle Map of a Soft Uniform Phantom

Simulation results in section 2.1 showed that the δ behavior resulting from Kelvin-Voigt model, the analytical method, Eq. (7), and the Evans' method, Eqs. (8-10), agree well in low frequency range, below about 0.4 Hz. To validate the Evans' method on a phantom, the same soft uniform phantom data from FIG. 4A were used.

In order to assess the appropriateness of Kelvin-Voigt model for detected slow creep deformations, quantifying the amount of deviation from this model is essential. The measured strain at a discrete time point $t_n$, n=1, N, can be expressed as $$d(t_n) = d_f(t_n) + e(t_n) \quad (11)$$

where $d(t_n)$ is the measured strain and $d_f(t_n)$ represents the fitted viscoelastic compliance curve based on the selected model. The term $e(t_n)$ describes the residual error. Eq. (12), therefore, represents the normalized error, where Q quantifies the goodness of the fit in terms of variance of the residual error, $e(t_n)$ relative to the total measured strain variance $$Q = \sqrt{\frac{\left\{\frac{\sum_{n=1}^{N}[d(t_n) - d_f(t_n)]^2}{N}\right\}}{\left\{\frac{\sum_{n=1}^{N}[d(t_n)]^2}{N}\right\}}} \quad (12)$$

Figure 5A:
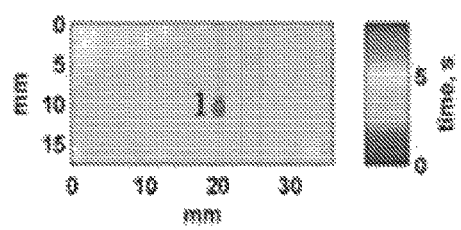
FIGS. 5A, 5B, 5C, 5D address δ behavior based on the analytical methods and the Evans' method.
Figure 5B:
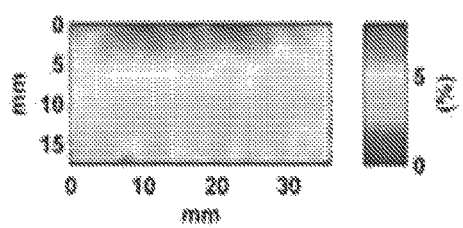
Figure 5C:
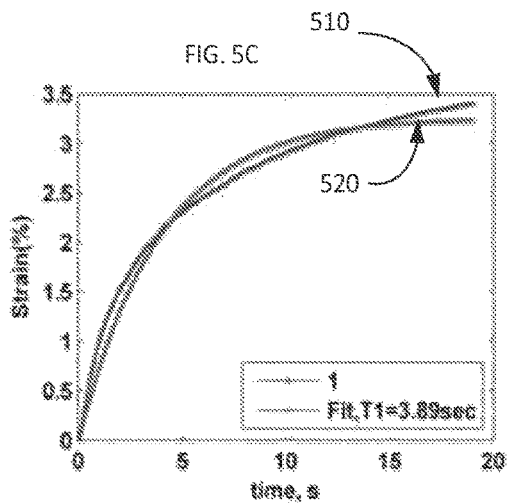
Figure 5D:
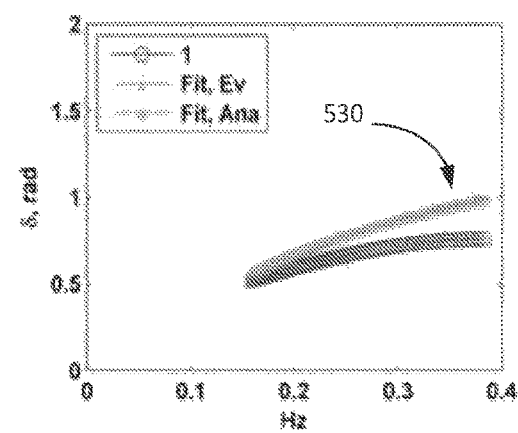

The advantage of measuring such error is that the model deviation can be measured regardless of the total strain value. FIG. 5A illustrates the $T_1$ map, while FIG. 5B illustrates the residual error map, according to Eq. (12). In FIG. 5C, the strain and its fitted curve profile of the point specified in FIG. 5A are shown. The resultant loss angle profile, δ, caused by applying Evans methods to strain data of the specified point in FIG. 5A (curve 510) accompanied by applying the Evans method on fitted curve (curve 520), and also analytical method on the fitted curve 520 (resulting in curve 530) are shown in FIG. 5D.

Figure 6A:
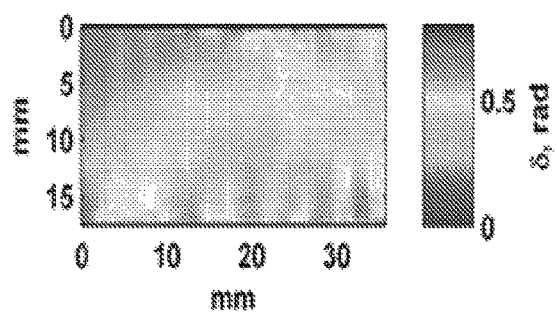
FIGS. 6A, 6B present maps for a soft uniform phantom and compare the δ behavior based on the Analytical methods and Evans method.
Figure 6B:
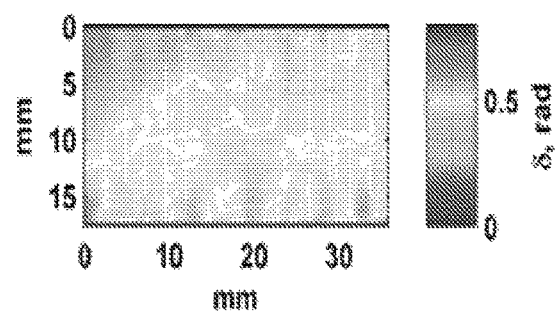

The same procedure is applied for all the points in a phantom to construct the δ map at 0.16 Hz, which is as is observed in FIGS. 6A and 6B. Here, the δ map of FIG. 6A is formed based on applying Evans method to the fitted curve of strain profiles of each point of the phantom. To obtain the δ map of FIG. 6B the analytical method is used on the same data. A further δ map can be obtained by applying the Evans methods to the strain profile of each point in the phantom.

In order to compare the results presented in the maps of FIGS. 6A, 6B, a relative error for each parameter is defined as follows $$E(\%) = \frac{T_D - T_u}{T_u} * 100 \quad (13)$$

In this Eq. (13), $T_D$ is the mean value of the values of the loss angle map obtained with the use of Evans method on the fitted curve; $T_B$ is either the mean value of the loss angle map obtained by applying Analytical methods to the fitted curve or the mean of the loss angle map obtained based on using Evans methods on strain profiles. The empirically determined relative error between the resultant Evans-based δ map of FIG. 6A and the analytical δ map of FIG. 6B) was smaller than 8%.

The procured results confirm that for the phantom data at frequency of 0.16 Hz the δ maps obtained with the use of Evans method and those obtained with the use of analytical method are substantially the same.

3.3.1 Loss Angle Map of an Inclusion Phantom

Figure 6C:
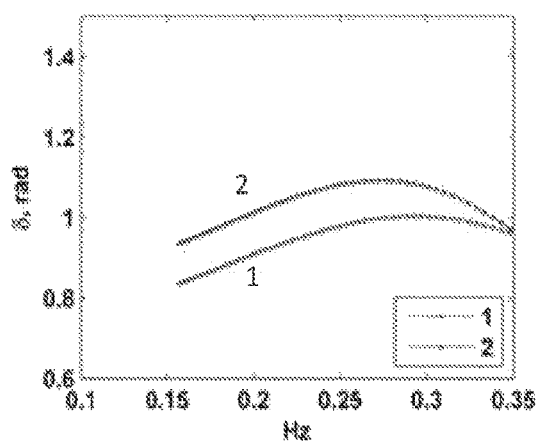
FIG. 6C includes plots illustrating δ profile for points 1 and 2 of FIG. 3A.
Figure 6D:
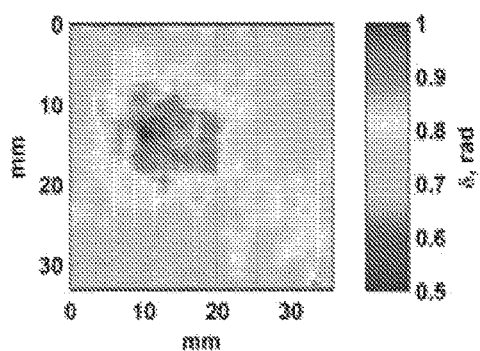
FIGS. 6D, 6E, 6F, and 6G present maps for loss angles obtained at frequencies below 0.3 Hz for three trials on inclusion phantom.
Figure 6E:
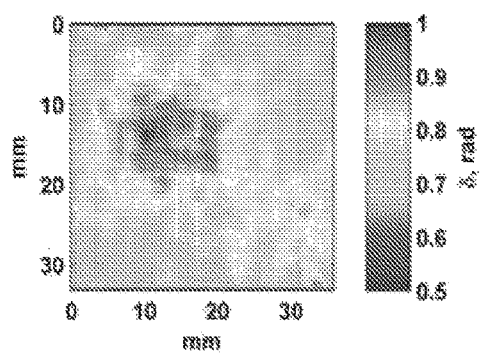
Figure 6F:
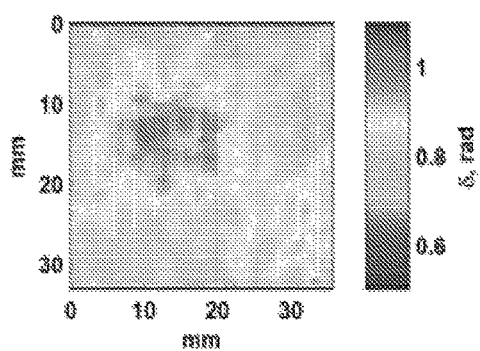
Figure 6G:
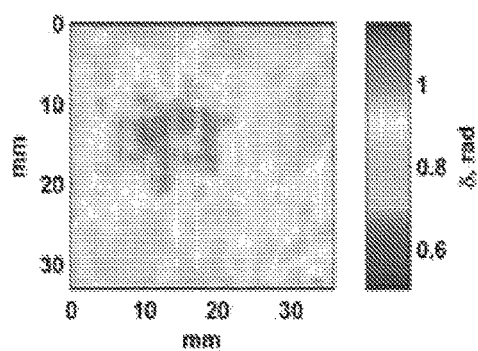

The same phantom data that used in the previous section to create the $T_1$ maps, FIGS. 4A through 4D, were further used to form the loss angle δ maps based on Evans method, Eqs. (8-10). The curves representing loss angles for the specified points 1 and 2 of the B-mode image of FIG. 3A are illustrated in FIG. 6C. For the inclusion phantom, which is stiffer, has lower strain (see FIG. 3B), and higher $T_1$ value (see FIG. 4C) at frequencies lower than 0.3 Hz, the δ values are elevated as compared to the background (which is softer with lower $T_1$ value). FIGS. 6D, 6E, 6F, and 6G illustrate the maps of the loss angle δ at frequencies below 0.3 Hz (at 0.16 Hz, at 0.19 Hz, at 0.23 Hz, and at 0.26 Hz, respectively) for several trials on inclusion phantom.

5. Comparison of Behavior of the Loss Angle δ in Sub-Hertz Frequency Range with Retardation Time $T_1$ Ideally, the retardation time $T_1$ should be estimated under a constant stress test, which is however impractical due to a sudden "shift" or "jump" in the value of stress applied to the target. In practice, this step-function is replaced by a ramp function, the extent of which should be accordingly excluded from the creep analysis.

Choosing the initial point in evaluation of the viscoelastic properties of the medium is a challenging part of measuring the retardation time, $T_1$. To determine the exact moment where the elastic response ends and the viscoelastic portion begins can be quite involved. At the beginning of the creep curve response, there is present a mix or combination of elastic and viscoelastic responses. These factors can affect the initial part of the creep response. Previously, the initial/beginning portion of the creep response was truncated or not considered to eliminate the confusion. The surface force profile resulting from the creep device was used as a tool to decide how big a beginning portion of the acquired creep response data had to be neglected/not counted. The moment when the force profile reaches the steady state is considered to be a moment when the viscoelastic response of the medium is initiated (or started). The following disclosure shows that the sensitivity of the loss angle δ to the choice of the initial point is much smaller than the retardation time in viscoelastic phantoms. The reason for it stems from the fact that sub-Hertz range of frequencies of the creep response is associated with the end of the creep response in time domain. The initial, beginning portion of the creep response—which is mostly related to high-frequency components—does not have a dominant effect on the δ value in the sub-Hertz frequency range.

Figure 7A:
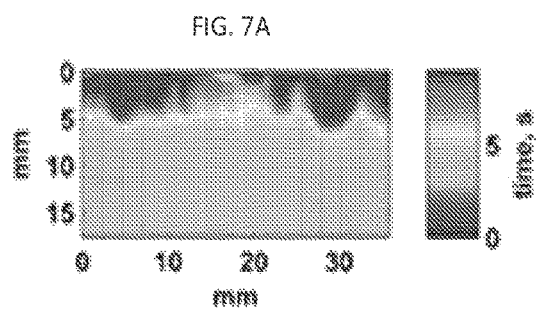
FIGS. 7A, 7B. 7C, and 7D: Retardation time maps, T1, for different cutting points in stiff and soft uniform phantoms (compare with FIGS. 4A, 4B).
Figure 7B:
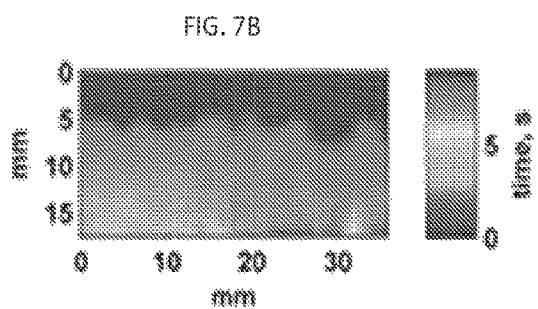
Figure 7C:
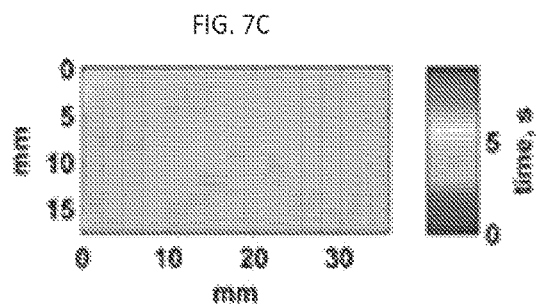
FIG. 7C: T1 map of soft uniform phantom with cutting point of 1 second.
Figure 7D:
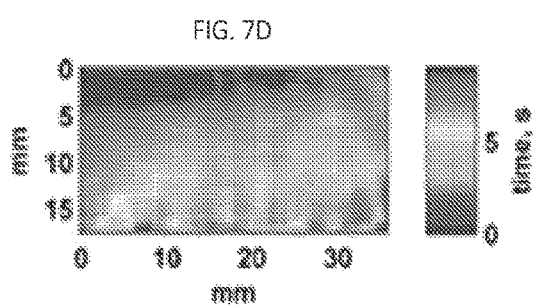
FIG. 7D: T1 map of soft uniform phantom with cutting point of 3 seconds. The retardation time map has been elevated in FIGS. 7B and 7D as compared with FIGS. 7A, 7C.

In comparison with FIGS. 4A, 4B, which illustrated the retardation maps of the stiff and soft uniform phantoms with the initial truncation point of 2 second, FIGS. 7A, 7C show the retardation time maps for the same two phantoms with a truncation time point of 1 second, while FIGS. 7B, 7D illustrate the retardation maps for the same two phantoms with truncation time of 3 seconds.

Figure 8A:
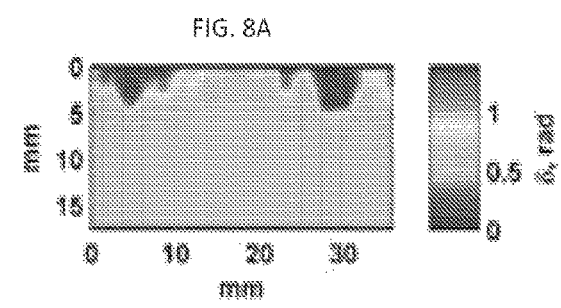
FIG. 8A: a δ map of stiff uniform phantom with a cutting (truncating) point of 1 second.
Figure 8B:
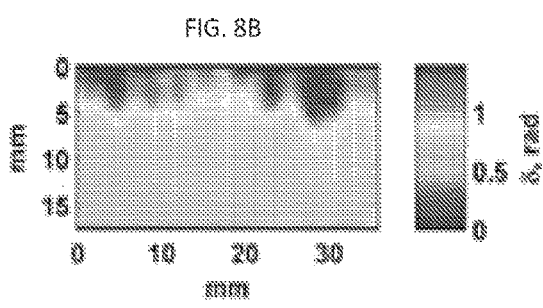
FIG. 8B: a δ map of stiff uniform phantom with a cutting point of 3 seconds.
Figure 8C:
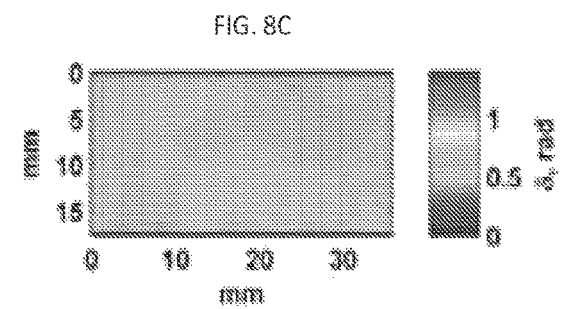
FIG. 8C: a δ map of soft uniform phantom with a cutting point of 1 second.
Figure 8D:
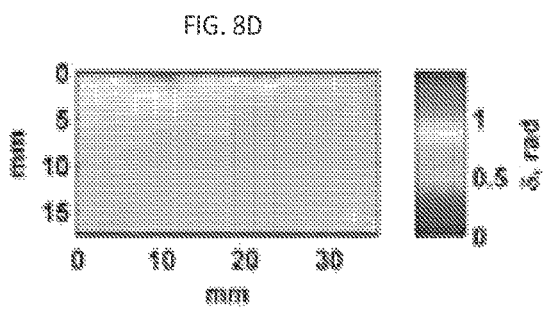
FIG. 8D: a δ map of soft uniform phantom with a cutting point of 3 seconds.
Figure 9A:
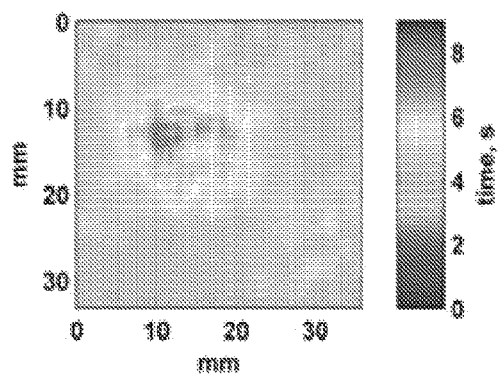
FIGS. 9A, 9B. Retardation time maps, T1, of an inclusion phantom, for different cutting points in inclusion phantom.

In the next steps, the δ maps were created based on Eqs. (8-10) for 0.17 Hz and the same truncation (cutting) time points as those of FIGS. 7A through 7D. These resulting maps are shown in FIGS. 9A through 8D, respectively.

Figure 9B:
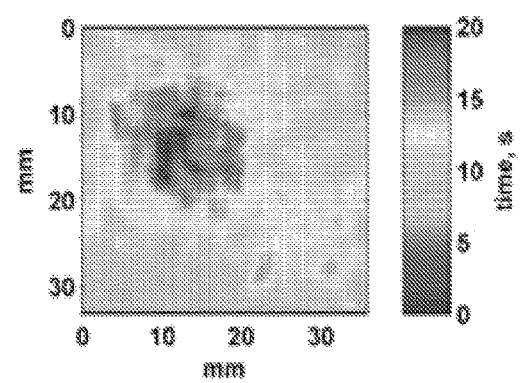
Figure 10A:
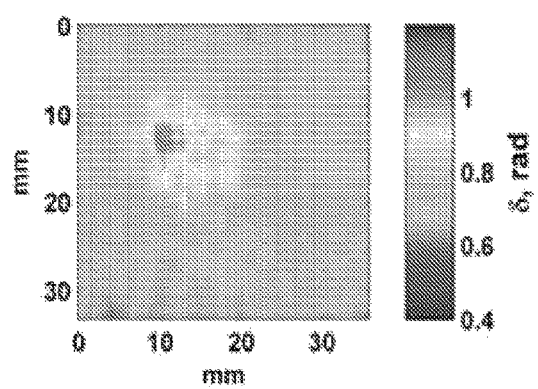
FIG. 10A: a cutting point of 1 second.
Figure 10B:
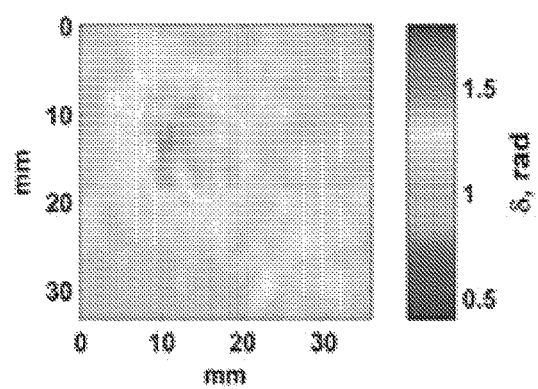
FIG. 10B: a cutting point of 3 seconds.

The same procedure has been repeated for the inclusion phantom. FIGS. 9A, 9B clearly indicate that the retardation time T1 is increased when the initial cutting (truncation) time point is changed. The error fit has been decreased by increasing the cutting point, but overall it is less than 10%. Following the determination of the retardation time maps, the δ maps with different initial cutting points were constructed for the inclusion phantom (at 0.17 Hz), FIGS. 10A, 10B, evidencing an increase of δ value with the increase of the cutting point.

4. Quantitative Comparison of Loss Angle Maps in Sub-Hertz Frequency Range with Retardations Time Maps with Different Initial Time Truncation Point.

Following the creating of the loss angle and retardation time maps for different phantoms. The amount of bias for the retardation time measurement and the loss angle measurement was determined based on Eq. (14):

$$BR=(MH-ML)/ML \quad (14)$$

where BR is the Bias Ratio, MH is the mean value of highest elimination frames (in our case it is the mean value of resulted maps with 3 seconds cutting points), and ML is the mean value of lowest elimination frames which is the resulting map with 1 second cutting point.

The results, summarized in Table 1, confirmed that the variation of the Bias Ratio for the loss angle in the sub-Hertz frequency range, for various kinds of phantoms is smaller as compared to that for the retardation time. The sensitivity of the loss angle calculation to initial cutting time in the sub-Hertz frequency range is, therefore, lower as compared to that of the $T_1$ value. In this range of frequencies (less than about 0.3 Hz), he high frequencies that are associated with the initial part of creep response are not involved (not accounted for).

TABLE 1

Bias Ratio, BR, for $T_1$ and δ measurement in different phantoms.

| BR | Soft uniform Phantom | Stiff uniform phantom | Inclusion phantom |
| --- | --- | --- | --- |
| T1 | 4.29 | 7.04 | 9.06 |
| δ | 0.16 | 0.12 | 0.4 |

5. Loss Angle Maps In Vivo

Figure 11A:
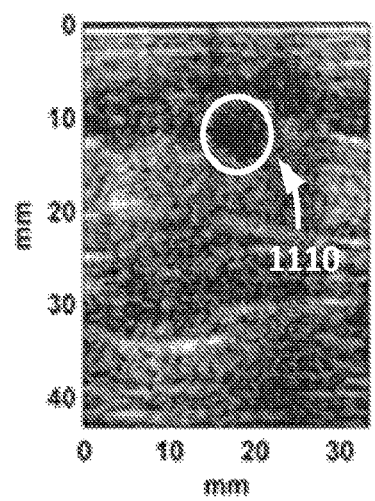
FIG. 11A: an ultrasound B-mode image of a breast tissue of a benign patient. The circle shows the location of the benign tumor.
Figure 11B:
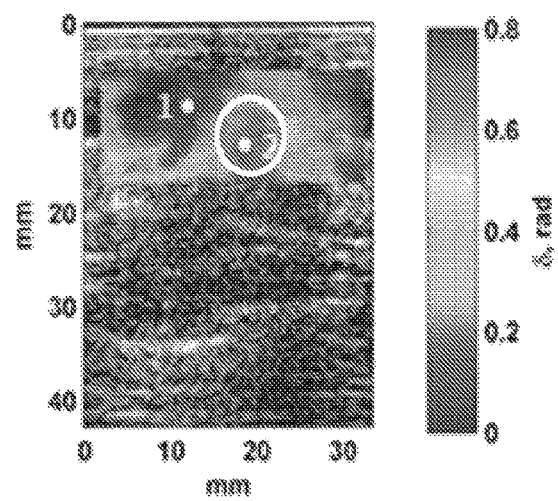
FIG. 11B: Registered δ map created at frequency 0.14 Hz for the benign patient.
Figure 12A:
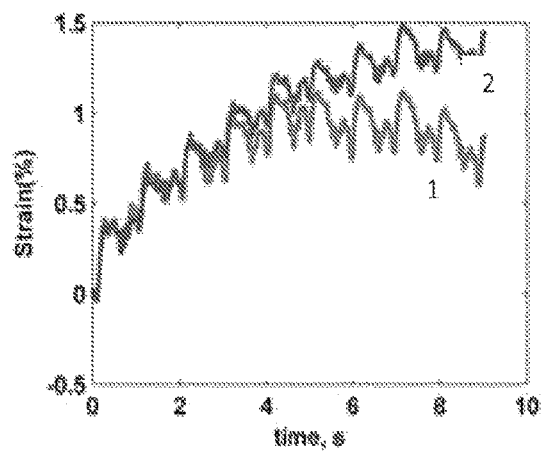
FIG. 12A: strain profile corresponding to points of tissue identified in FIG. 11B.
Figure 12B:
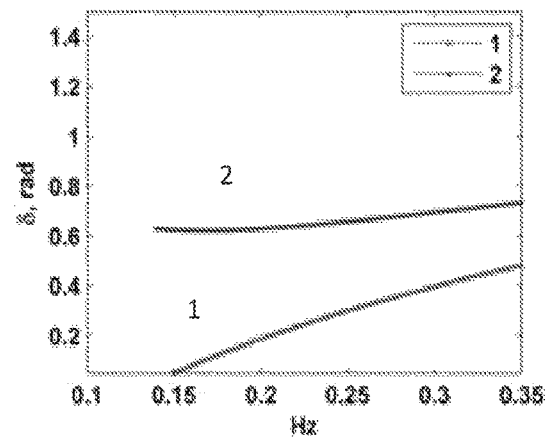
FIG. 12B: loss angle profiles corresponding to the same identified points.
Figure 13A:
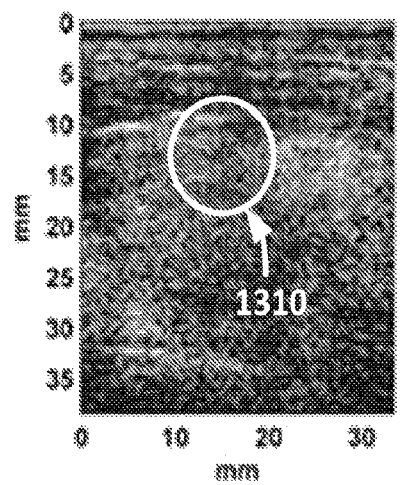
FIG. 13A: an ultrasound B-mode image of a breast tissue for a malignant case. The circle shows the location of the tumor, FIG. 13B includes a registered loss angle map.
Figure 13B:
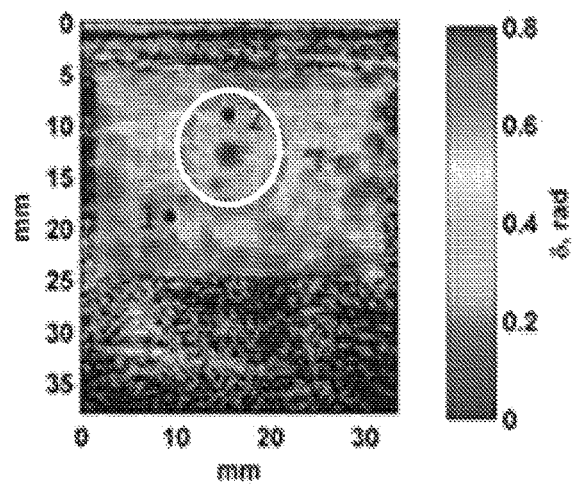
Figure 14A:
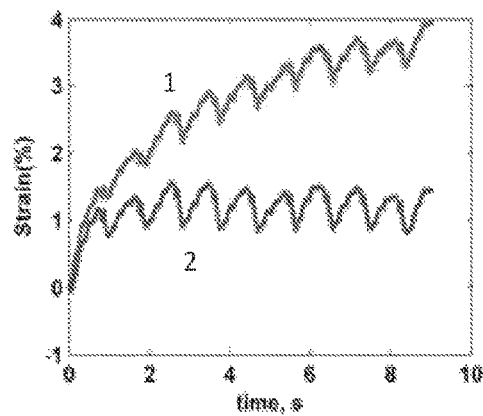
FIG. 14A: strain profile corresponding to points 1 and 2 identified in FIG. 13B.
Figure 14B:
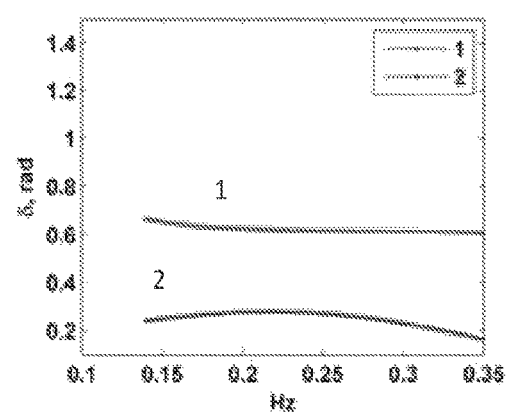
FIG. 14B: loss angle profiles corresponding to points 1 and 2.

The data were acquired from 2 female patients, pre-screened by mammography. After the study each patient went for the core needle biopsy procedure. FIGS. 11A, 11B show the ultrasound (B-mode) image and the δ map (at 0.14 Hz) co-registered with the B-mode image of a benign patient. The circle 1110 shows the location of the benign tumor. The benign lesion 1110 shows a higher δ value as compared to the background. FIGS. 12A, 12B depict in more detail the behavior of two specified points, 1 and 2 of the tissue (inside and outside of the benign tumor). Specifically, FIG. 12A shows the strain at these points, evidencing that the background strain is lower than the strain at the benign tumor (which means the tumor is softer than the background due to tumor's higher strain), while FIG. 12B illustrates their behavior in the frequency range of less than 0.35 Hz. The δ profile of FIG. 12B is elevated for the lesion as compared to that for the background in the frequency range below 0.3 Hz. The same process was repeated for another patient with a malignant tumor, indicted in the B-mode image as 1310. FIG. 13B shows a co-registered loss angle map for this case. In a fashion similar to that of a benign case, the temporal and spectral behavior of the two points at the tissue inside and outside of the malignant tumor are compared in FIGS. 14A, 14B. At low frequency ranges the δ value is lower for a malignant tumor tissue as compared to the background tissue, while for benign case the δ value for tumor is higher as compared to that of the background tissue.

6. Parametric Contrast Measurements

Measuring contrast characteristics is important for facilitation of diagnostics/status of the target object. Contrast of a given map was determined according to Eq. (15), below:

$$\text{Contrast} = \left(\frac{\text{Difference}}{\text{Average}}\right)$$

=2(Lesion Value−Background Value)/(Background Value)

Figure 25:
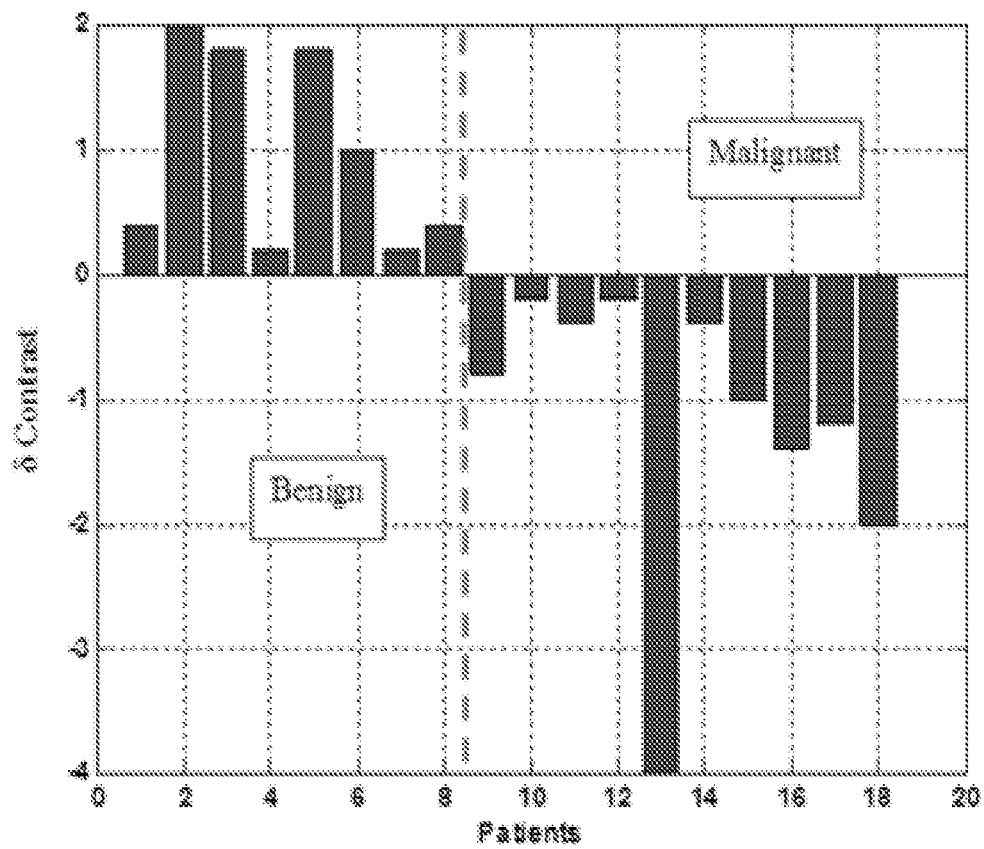
FIG. 25 is a bar graph depicting the sign of contrast, determined for the loss-angle maps for 18 subjects (positive δ-map contrast indicates benign lesions; negative δ-map contrast indicates malignant lesions).

Here, the Lesion Value is the mean value of loss angle in a lesion-containing part of the tissue, while the Background Value represents the loss angle value of the background in the phantom or tissue. It is appreciated, therefore, that differentiation between the malignant and benign lesions can be carried out based on the determination of the value of the parametric contrast. According to Eq. (15), the measured contrast of the δ-map for the benign lesion case (FIG. 11B) is 1.8, while for the malignant lesion case (FIG. 13B), is −0.4. A more diverse experimental study, performed with multiple patients (breast tissue), resulted in the statistics reflected in FIG. 25.

FIG. 15A shows the loss angle map of the inclusion phantom, FIG. 15B illustrates the quality mask map, while FIGS. 15C, 15D represent the mask applied to measure mean value inclusion portion and the and background portion respectively.

We defined a parameter as quality mask measurement in order to evaluate the strain/stress behavior of each point in the medium while applying compression. Sometimes due to fluidic nature of a part of the medium or tissue, the strain behavior of such part is negative. FIG. 15A illustrates the loss angle map. The quality mask (FIG. 15B), is constructed based on the evaluation of the loss angle sign, so various "well-behaved" situations are considered to have a value of one, while the misbehaved situations are assigned a value of zero. FIG. 15B illustrates the quality mask, while FIG. 15C shows lesion mask for measuring loss angle of the inclusion part of the phantom. FIG. 15D is a background mask.

The behavior of the strain profiles and loss angle profiles is illustrated in FIGS. 16A, 16B, respectively. In this inclusion phantom study, all points have well behaved strain profiles. Loss angle in misbehaved situations turns negative at low frequencies.

It has been demonstrated, therefore, that measurement of the phase difference between relative storage and loss modulus based on temporal strain profile in frequency domain (to observe the contrast in the medium due to its viscoelastic properties in sub-Hertz frequency range) can be efficiently carried out with the use of a loss angle. The loss-angle-based method is a model-independent method, in which no curve fitting is required, which allows the determination of the phase difference to be performed with higher accuracy/precision, as compared to the methods of the related art. The determination based on the loss angle utilizes experimental data directly, without fitting such data to any model or function. The applicability of the loss-angle based determination was corroborated with the use of the Kevin-Voight approach (conventionally used for simulation and characterization of the creep response in tissue mimicking phantoms) within the low frequency range below 0.3 Hz.

It should be noted that when it comes to creep response, the determination of the distribution of local stress inside the compressed medium remains the main challenge for conventionally-employed methodologies: for example, the determination of such distribution based on forward methods has not been realized and is rather questionable (H. Eskandari et al., "Viscoelastic characterization of soft tissue from dynamic finite element models," Physics in medicine and biology, vol. 53, p. 6569, 2008). Due to this ambiguity of identifying/assessing the internal stress distribution in the medium, it is not possible to quantify the Young's modulus based on these methods, either. Thus all the parameters that can be extracted from strain profiles with the use of conventional methods remain relative, not exact. This is the reason that in frequency domain, the measured storage and loss modulus are relative. However, when it comes to measuring the phase difference between the storage and loss moduli, the value of tangent of the loss angle, the effect of the stress distribution is eliminated (see C. Amador et al., "Loss tangent and complex modulus estimated by acoustic radiation force creep and shear wave dispersion," Physics in medicine and biology, vol. 57, p. 1263, 2012). It is this fact that the idea of the present invention takes advantage of.

As was discussed above, based on the implementation of the idea of the invention, the results of the phantom study (FIGS. 4A through 4D) and actual patient study (FIGS. 12A, 12B, 14A, 14B) evidenced that the loss angle profiles (which relate to the creep responses of the points inside and outside of the inclusion in the target tissue) provide good contrast between the inclusion part and background part in frequency ranges less than about 0.3 Hz, because of the difference in viscoelastic properties of the inclusion portion of the tissue and the background portion of the tissue. The evaluation of the viscoelastic creep response of the medium in the frequency domain based on the loss angle, δ, in sub-Hertz frequency ranges have some certain advantages as compared to retardation time measurement, T1, in the time domain, at least because of empirically-demonstrated lower sensitivity of the loss angle to the initial truncation time point. Additionally, the advantageous low computational cost comparing to retardation time methods should not be ignored. The in vivo results indicated that the loss-angle-based method has the ability to differentiate between benign and malignant tumors in our case study.

Appendix A: An Automated Compression Device for Use in Tissue Viscoelasticity Imaging As has been already alluded to above, mechanical properties of the medium can be assessed by creep test. Creep test is a standard method to evaluate the continuous deformation of a material under a constant stress, and the creep response of a material is the result of applying a step-force excitation to the material. (Such force causes a transient strain response that is governed by the viscoelastic properties of the material.) To use creep test in different imaging modalities such as ultrasound, various compression devices have been designed. For example, hand-held compression method has been discussed, but manual compression is usually accompanied with noise due to hand jitter, which may reduce the reproducibility and repeatability of this method.

Since the subject of the described above investigation is viscous response of the tissue, the study of the temporal response of tissue under constant stress was required. Below is discussed a fully automatic device (used to conduct the above-disclosed experiments) with the ability to apply an approximate step force to excite the viscoelastic creep response in tissue while allowing in-vivo ultrasound image acquisition during the transient response of tissue. To validate the device, its performance is compared with a standard, conventionally-used mechanical testing device and measurement of the related error.

Under external stress, material deformation can be modeled using the constitutive equations from continuum mechanics. Simplified models such as generalized Kelvin model are shown to be suitable in the case of uni-axial constant stress on hydrogels and their creep responses are shown to be close to those of soft tissue. For each point inside the material the strain-stress relationship is $$\varepsilon(t) = \int_{t_0}^{t} D(t-\tau) d\sigma(\tau) \quad (A.1)$$

Where $\sigma(\tau)$ is the applied stress, $D(\tau)$ is the creep compliance, and $\varepsilon(\tau)$ is the resulting strain. Employing the generalized Kelvin model (R. Righetti et al., in *Ultrasound in medicine & biology*, vol. 30, pp. 215-228, 2004), expressing the stress applied to the tissue at $t=t_0$ with the use of the Heaviside function, the general creep response $\varepsilon(t)$ can be expressed as the sum of the elastic response $\varepsilon_0$ and the contribution of the viscoelastic terms. When using a second-order Kelvin-Voigt rheological model, the creep response can be expressed in terms of two retardations times T1 and T2 and corresponding response amplitudes $\varepsilon_1$, $\varepsilon_2$ as $$\varepsilon(t) = \varepsilon_1 \left(1 - \exp\left(-\frac{t}{T_1}\right)\right) + \varepsilon_2 \left(1 - \exp\left(-\frac{t}{T_2}\right)\right) \quad (A.2)$$

While the creep test requires the application of a step-force, t is not possible in practice to apply a step force to the target and study its response. It is, however, possible to approximate the step force with a ramp-and-hold force, where the speed of the ramp is adjusted to suite the response of the material under test. The ramp speed should be chosen fast enough such that the initial elastic response of material can be easily separated from the slow creep response and can be considered as a step instead of ramp.

With that in mind, in almost all commercial mechanical testing machines the theoretical step stress required for the creep test was replaced by a highly controlled ramp function. However, the speed of such ramp stress should be ensured to be high enough to be able to capture the shortest retardation times of the material under the test. According to the idea of this invention, a compression device is devised that is able to create such ramp forces, with the additional feature of housing an ultrasound probe for continuous strain imaging during the test.

Figure 17:
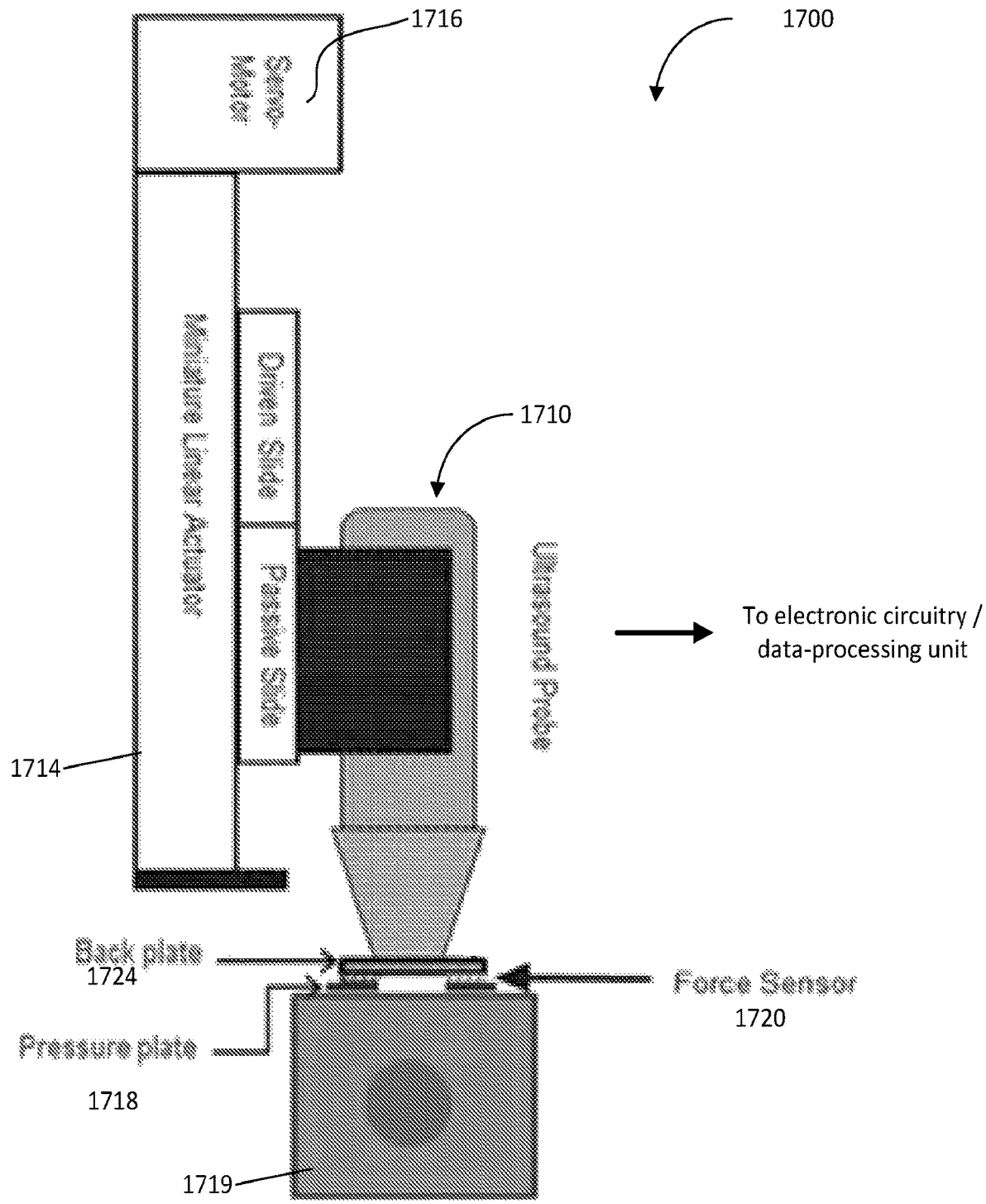
FIG. 17 is a schematic diagram of an automated compression device employed for measurements/creep test

A schematic of an embodiment of the device, configured according to the idea of the invention, is shown in FIG. 17. The embodiment 1700 is equipped with an ultrasound probe 1710, which is configured to record local deformation of target (tissue) under stress. This device includes a light-weight, miniature linear actuator 1714 (in one implementation—MR20LS with 2 mm lead screw, PBC Linear, Roscoe, IL), driven by a brushless DC (BLDC) servomotor 1716, (RP17M brushless DC servomotor with encoder, Electrocraft, Dover, NH), which in operation moves a commercial ultrasound probe 1710 together with a pressure plate 1718 rapidly onto the material or tissue 1719 until a preset force level on the probe face is reached. In one implementation, the actuator control system uses 4 small load sensors 1720 (FSS015, 15 Newton range, Honeywell, Bloomington, MN), embedded in a back plate, to measure the applied force. The control system maintains the preset force level constant for a predetermined period of time, typically about 10-100 seconds. When the creep measurement is complete, the actuator 1714 automatically retracts the probe.

Figure 18:
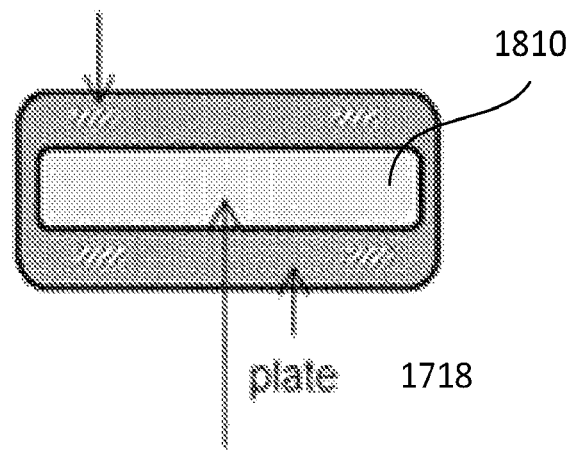
FIG. 18: spatial coordination of the surface of the probe of FIG. 17 and the pressure plate as well as 4 force sensors positioned at the 4 corners of the pressure plate; in front view; includes the pressure plate with membrane. The load cells are located between the pressure plate and the back plate (not seen in FIG. 18).

The back plate 1724 is custom fit to the probe 1710 using a liquid castable plastic material (such as, for example, SmoothCast 300, Smooth-on. Inc., Easton, PA). The four small load sensors 1720 are sandwiched between the back plate and the pressure plate. FIG. 18 illustrates the position of the load sensors 1720 at the 4 corners of the pressure plate 1718. Consequently, as the motor of the system keeps compressing the object (target), the resulting resisting force from the object is transferred to the load sensors 1720 through the pressure plate 1718. There is (an optionally approximately rectangular) opening 1810 at the center of both pressure and back plates dimensioned to allow the face of the probe 1710 to move though the plate(s) such that the probe face stays at the same level as the pressure plate 1718. This opening 1810 is covered with a thin acoustically-transparent membrane that transmits the ultrasound beams.

As shown, the four load sensors 1720 are symmetrically located at the four corners of the plates 1718, 1724. The total force is then calculated, with the use of the operably-cooperated with the system 1700 programmable computer processor, by averaging the outputs of the sensors 1720. The solid pressure plate 1718 transfers pressure from the medium/target/tissue to the load sensors 1720. Non-uniform contact between the pressure plate and the medium/target may result in unequal loading on the sensors. However, because the outputs of the sensors are averaged, the total output will still correspond to the total force applied to the medium. The overall dimensions of the device, in one embodiment, is 31 cm×7 cm×5.5 cm (length×width×depth).

Figure 19:
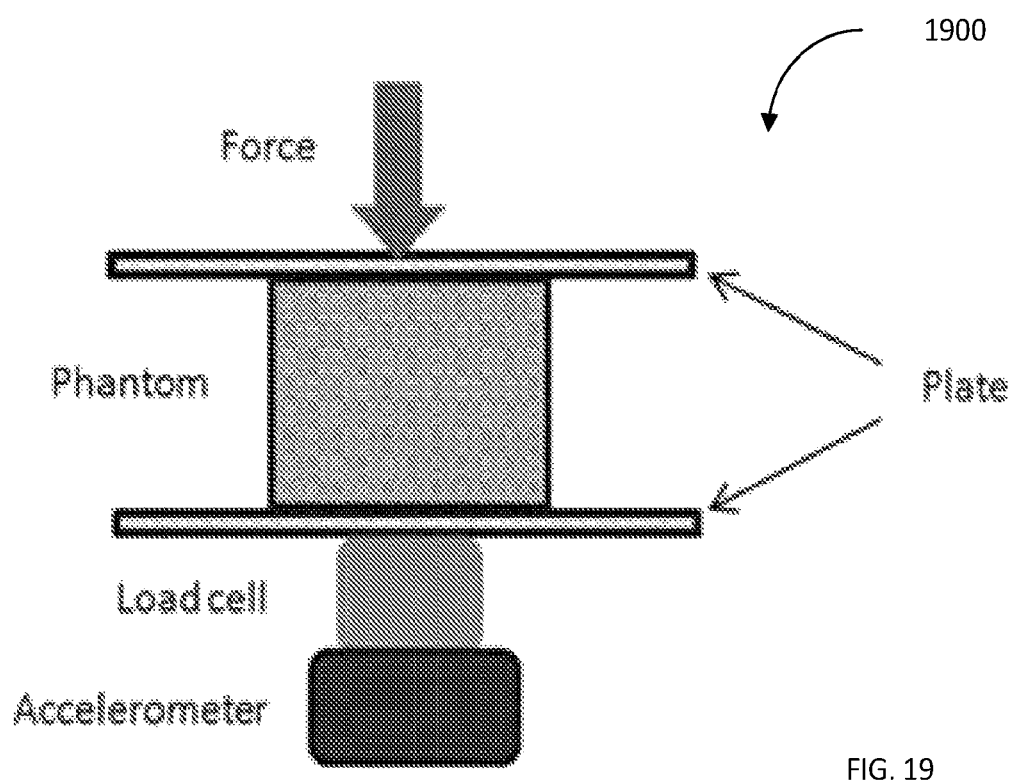
FIG. 19 provides a schematic of the Bose instrument including two plates, sandwiching the target in-between, and the force applied to the top plate. There is a load cell at the bottom of the instrument to measure the force transferred to the target/phantom and an accelerometer at the bottom of the load cell to compensate for the inertia.

The validation of the compression device 1700 was carried out with the use of a standard mechanical testing instrument (Bose ElectroForce®, Eden Prairie, MN; see schematic 1900 in FIG. 19) to apply force and record the resulting displacement and repeated the same procedure with automated compression device 1700; the results obtained with these two devices were then compared. In particular, the forcing function in the form of ramp-and-hold with 3 N final force and 18 N/s ramp rate (ramp duration of ⅙ seconds) was used. In one implementation, the 18 N/s ramp is the upper limit of the speed that could still ensure that no ringing effects would be caused in the gelatin phantoms used in the experiments.

Creep tests, discussed above, were performed on a homogenous tissue-mimicking phantom. To construct phantom, 13.7 grams gelatin (Sigma-Aldrich, St. Louis, MO), 60 mL Vanicream Lite (Pharmaceutical Specialties, Inc., Rochester, MN), 0.3 grams of agar (A5306, Sigma-Aldrich), 3 grams cellulose (Sigma-Aldrich) for ultrasound scattering and 3 grams potassium sorbate (Sigma-Aldrich) as a preservative, were dissolved in enough water to make the total solution volume equal 300 mL. Phantom dimensions, in one implementation, were 4×6×2 cm (length×width×height). The same phantom was tested with devices of FIGS. 17 and 19, with similar force and ramp functions. The surface displacement data acquired with the Bose system of FIG. 19 and those acquired with the compression device 1700 were recorded for 85 seconds.

Notably, phantom dimensions were smaller than those of the pressure plate in the compression device 1700 and also smaller than those of the plate(s) of the Bose instrument; therefore, the compression was applied similarly on the entire top surface of the phantom in both cases. This allowed for minimal boundary condition effects and thus the results would be comparable for both machines. There were no slippery boundaries involved. FIGS. 20A, 20B illustrate the load (force sensor output) from the device 1700 the Bose instrument 1900 at force level of 3 N with 18 N/s ramp speed. FIG. 20A shows the entire force signal. In FIG. 20B, just the initial 10 seconds is depicted. Both devices reach their final force values in a fraction of second. The substantially-coincident plots of FIGS. 20A, 20B evidenced the coincident of experimental results obtained with these two different systems.

The comparison between the results of the measurement of the retardation time of a test phantom with the use of the device 1700 and those acquired with the use of the device 1900 were also performed (for this purpose, measured was the surface displacement of the phantom). Since the applied force is not a pure step function, the initial part of the response is a complicated mixture of the elastic and viscoelastic responses to the ramp excitation. However, after the force reaches its final value, it is safe to assume that the time varying part of the strain profile is only due to viscoelastic response. For this reason, the initial part of the response is excluded from the strain data analysis and the model is reduced to a second order Kelvin-Voigt model. FIGS. 21A, 21B, 21C illustrate the surface displacement profiles assessed before and after fitting a curve according to Eq. (A.2). A nonlinear least square optimization method was used to find the closest fit to measure the two retardation times $T_1$ and $T_2$.

The suitability of Kelvin-Voigt model for observed slow creep deformations, as shown in Eq. (A.2), was also assessed by quantifying the amount of deviation from this model based on the figure of merit representing an error (for example, a variance of residual error) between the fit of the acquired data and the data themselves, quantified regardless of the total strain value. It was experimentally shown, with the use of the displacement data of FIGS. 21A, 21B, 21C, that error of 0.52% was characteristic for the Bose instrument response and that of 0.86% was typical for the compression device response. To test measurement reproducibility, the same experiments were five times on the same phantom using the same force, 3 N, and ramp speed, 18 N/s. Table A.I shows the resulting $T_1$ and $T_2$ values for these measurements.

TABLE A.I

Retardation time results for five trials on the same phantom with the same amount of force and ramp speed for both the compression device and Bose instrument.

| Measurement method | Retardation times T1 and T2 in seconds | | | | | | |
|---|---|---|---|---|---|---|---|
| | First | Second | Third | Fourth | Fifth | Average | Standard deviation |
| BOSE T1 (s) | 3.4 | 3.4 | 3.5 | 3.5 | 3.4 | 3.44 | 0.05 |
| Device T1 (s) | 3.6 | 3.2 | 3.4 | 3.2 | 3.4 | 3.32 | 0.17 |
| BOSE T2 (s) | 37.5 | 39.8 | 37.8 | 37.4 | 37.3 | 37.96 | 1.04 |
| Device T2 (s) | 33.8 | 31.8 | 34.9 | 32.4 | 33.8 | 33.34 | 1.24 |

Based on the average results of 5 trials, the percent error for $T_1$ and $T_2$ were −3.49% and −12%, respectively. These results indicate a strong agreement between the creep device configured according to the embodiment 1700 and the conventionally-used Bose instrument 1900.

Figure 22:
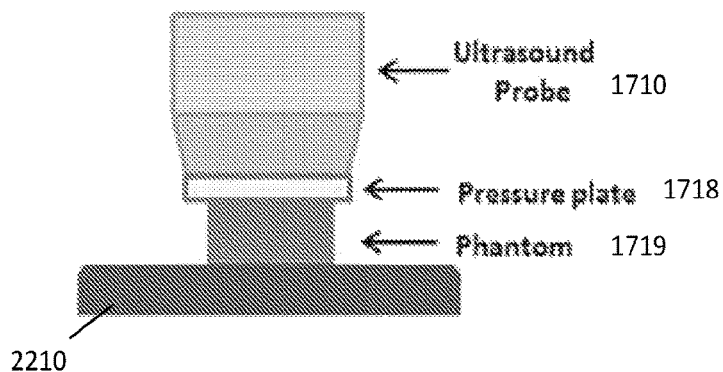
FIG. 22 provides a block diagram showing the location of the probe, pressure plate and phantom positioned on a base/support.

The application of the compression device 1900 combined with ultrasound strain imaging was further demonstrated for viscoelasticity evaluation of a medium. The first step in retardation time imaging is acquiring IQ data, analytic (complex) RF data, of the phantom that is being compressed by the compression device. Next, these data are used to calculate the strain at every pixel. Then the retardation time at each pixel is estimated to produce an image depicting the retardation distribution across the phantom. FIG. 22 shows the block diagram of the ultrasound probe 1710, pressure plate 1718, and the location of the phantom 1719 (on a base/support 2210) used for such determination.

It is appreciated, therefore, that an embodiment of the automated compression device is configured according to the idea of the invention to apply a prescribed amount of force, for a predetermined time, to a target such as tissue (or phantom) to characterize its mechanical behavior or creep response as a function of time. The results of such characterization are used further for imaging the viscoelasticity of the tissue (for example, breast tissue in a group of patients).

An important element of the embodiment 1700 of the device is the pressure plate complemented with four sensors symmetrically disposed at the corners of the plate. Output signals from these sensors are summed, to enable the sensor to measure the total applied force aggregately (collectively). Therefore, even in cases where the compression plate does not make complete contact with the surface of the object/target (for example, when the object's surface is not completely flat), the system is still enabled to measure the total force applied to the contact surface. Another important design feature of this device is the location of the load cells or sensors: they are disposed at the surface of the probe, which means that they can directly measure the force applied to the medium/target, regardless of presence and/or influence of the mass and inertia of the probe during the force measurement. The ability of the embodiment to measure the force and the surface displacement profiles is another important feature.

Figure 23:
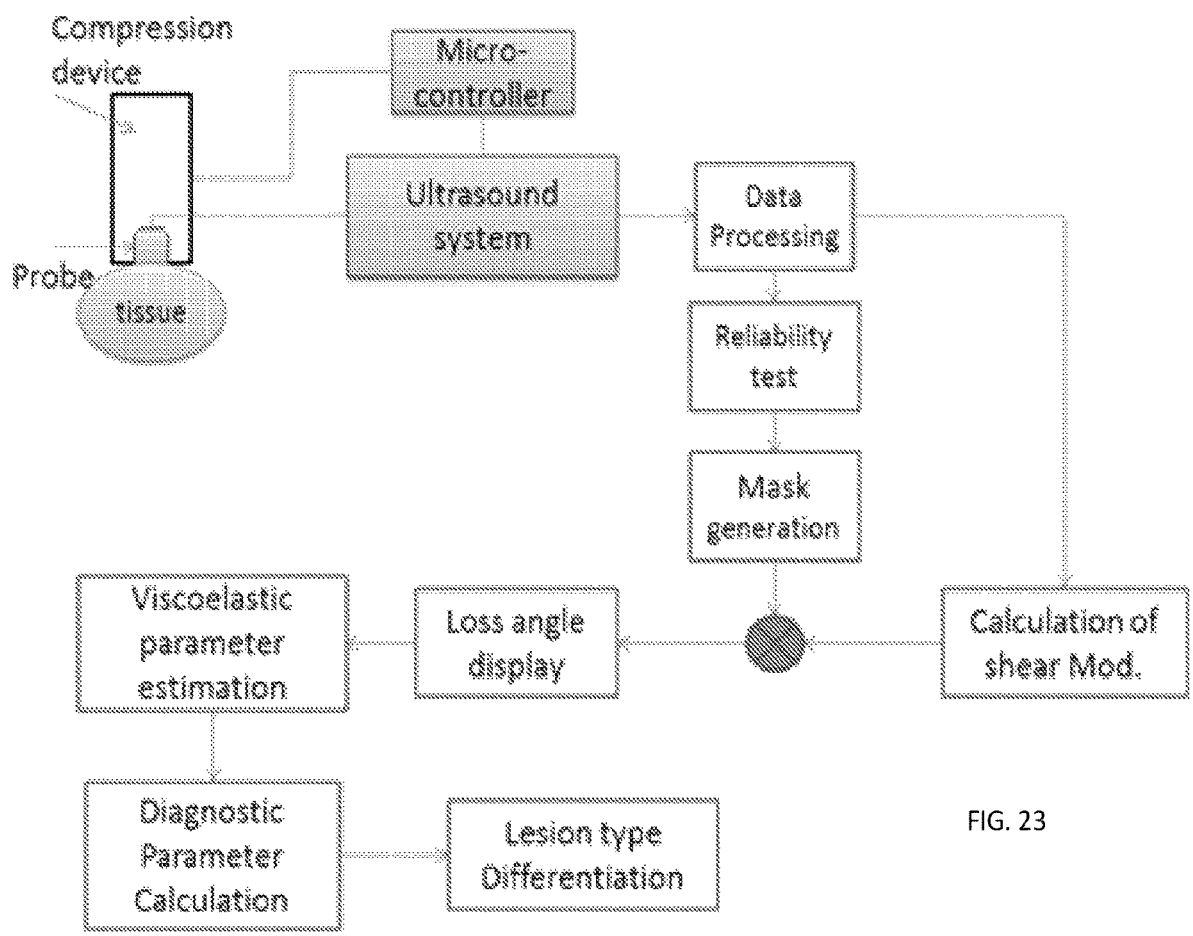
FIG. 23 is a schematic diagram of a measurement system configured according to an embodiment of the invention.

A person of ordinary skill in the art will readily understand, therefore, that the system for compression of a target object (such as a biological tissue, for example breast tissue) configured according to an embodiment of the invention includes: (i) a compression device configured to apply a force to the target object (such compression device is configured to vary an amount of force at a constant rate from an initial amount to the final predetermined amount, and, once the final predetermined amount is reached, to maintain said force at a substantially constant level); (ii) an ultrasound probe, with a transducer, mechanically associated with the compression device and configured to acquire radio-frequency image data frames (which represent a region of interest (ROI) of said target object, during a duration of time while the compression device holds the ultrasound probe in contact with the target object and while said force is being applied to the target object); (iii) an ultrasound imaging system cooperated with the ultrasound probe and configured to record a sequence of the image data frames during the duration of time; (iv) a compression device controller, operably cooperated with the compression device and including electronic circuitry programmed to set and control the constant rate (at which the force is applied) and to synchronize an operation of the compression device with an operation of the ultrasound imaging system; and (v) a data-processing unit configured to receive signal outputs produced at least by the ultrasound imaging system and the compression device controller to determine, based on such signal outputs, a value of local strain of the target object at each target object point that has been imaged, with the ultrasound imaging probe, as a function of time. A schematic diagram of such embodiment of the system is presented in FIG. 23.

The data-processing unit may be further configured to identify, based on said sequence of image frames and a signal output from the ultrasound imaging system, a target object location where a time-dependence of said value of local strain/stress does not follow a trend expected for a viscoelastic medium, by (i) identifying a sign of a slope of said time-dependence, and (ii) assigning a marker of unreliability to a portion of acquired data corresponding to a portion of the curve that has a negative sign. A method of so-identifying a specific target object location, carried out with the system of the invention, results in test of reliability of data acquisition process.

The data-processing unit may be further configured to filter out, from the signal outputs produced at least by the ultrasound imaging system and the compression device controller, an interference signal caused by an influence of at least one of a cardiac pulsation, breathing motion, residual effect of initial ramping of the compression device, and noise by processing said signal outputs within a frequency range that is devoid of such interference signal. For example, to reject or filter out influence of both cardiac pulsation (a first frequency band about 1 Hz) and breathing motion (a second frequency band about 0.2-0.33 Hz), the data-processing unit is configured to reject signals in the frequency band combining the first and second frequency bands to calculate a complex shear modulus G($\omega$) of the target object in the sub-Hertz frequency band excluding the first and second frequency bands.

In a specific embodiment, the system is further configured to determine a viscoelastic parameter of the target object in the frequency domain based at least in part on a dependency of the value of local strain as the function of time.

In a related embodiment, the system is further configured to determine a value of loss angle parameter as a ratio of real and imaginary parts of a complex shear modulus of the target object that has been assessed independently from distribution of stress in the target object, where the distribution of strain or stress having been caused by the force applied to the target object with the use of the compression device, and where the determination of the loss angle parameter is carried out in a range of frequencies defined to allow a determination of viscoelasticity of the target object with the use of the data-processing unit as a function of frequency. Alternatively or in addition, the system is configured to determine a tangent of the loss angle parameter, optionally within the range of frequencies defined to allow a determination of viscoelasticity of the target object as a function of frequency. Alternatively or in addition, the ultrasound imaging system is configured to display a map of the loss angle parameter as a color overlay over an image of the target object procured in B-mode of operation of the ultrasound probe.

In a specific implementation, the ultrasound imaging system is configured to record the sequence of image frames, each image frame representing a 2D image of the target object. In a related embodiment, the ultrasound imaging system is configured to record the sequence if image frames each representing a 3D image of the target object and generate a signal output further used by the data-processing unit to determine the loss angle in 3D space.

Figure 24:
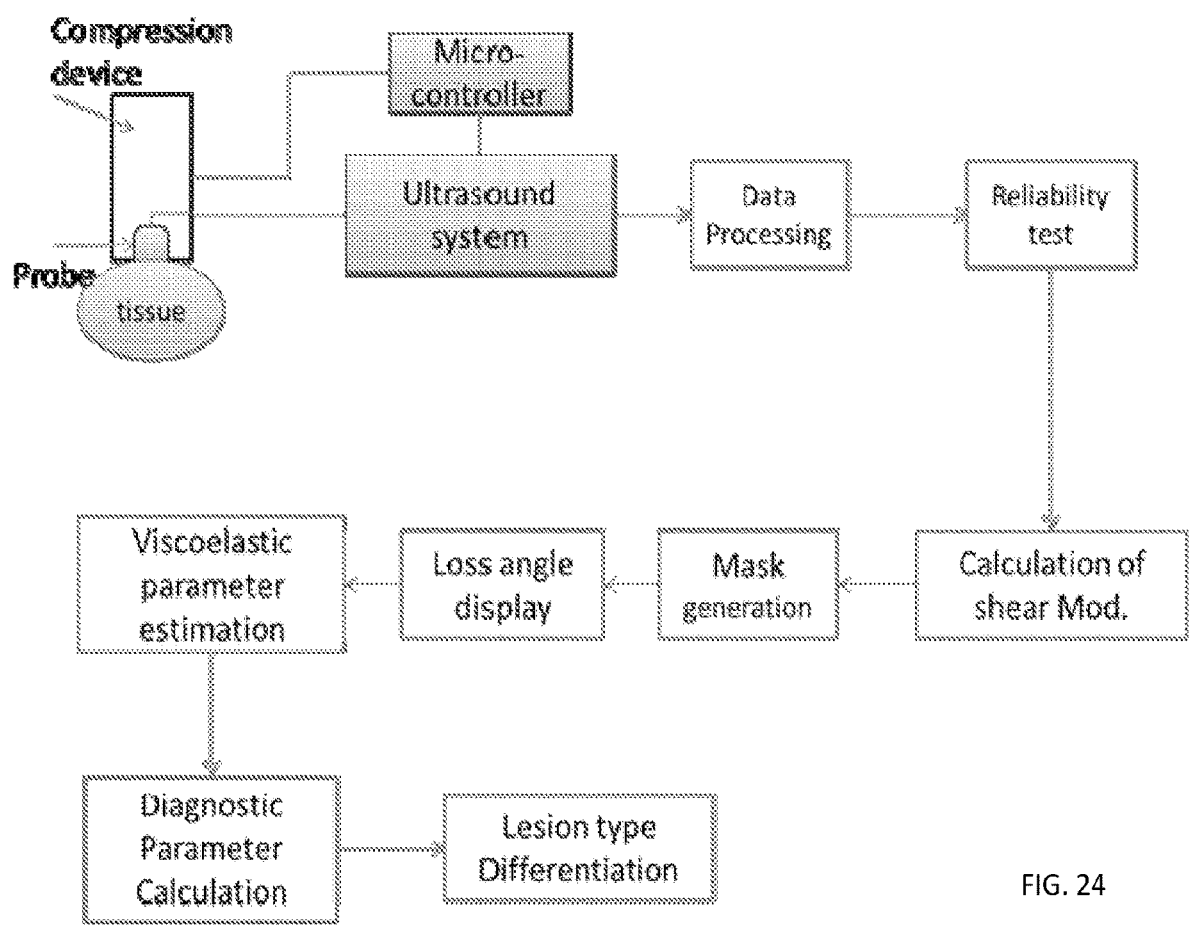
FIG. 24 is a schematic diagram of a measurement system configured to identify a region of a medium (e.g., tissue) that does not behave like a viscoelastic region.

A related embodiment of the ultrasound imaging based methodology of the invention, configured for determination of viscoelastic characteristic(s) of the targeted object (such as biological tissue) based on the assessment of the loss angle (carried out independently from distribution of stress, caused in the target object by application of force with the compression device) is shown in FIG. 24.

The embodiment of the system/method schematically illustrated in FIG. 24, for example, is configured to identify regions of the target object (medium) that do not behave like a simple viscoelastic material. Such system can be used to facilitate the detection of pockets of fluids in an otherwise viscoelastic medium, or detection of cysts in soft tissues. (Mechanical properties of fluids are significantly different from those of not fluid portion of the tissue, and fluids do not respond to the external compression in the same fashion as soft tissue itself. Accordingly, the local strain in the fluid region such as cyst caused by the application of force with the compression device differs from that of the surrounding medium. This difference in responses of the portions of the medium is used, according to one embodiment of the invention, to detect fluid pockets in the medium. The system of FIG. 24 utilizes the compression device, ultrasound system, data-processing unit and reliability test unit that are similar to those discussed above. The difference here that it uses the results of the "reliability test" to identify a region with a fluid or any other material that does not behave, in response to the applied compression force, in the same fashion as the surrounding viscoelastic material. The data produced by the "reliability test" module is then used to make a map (image) of the region. This map can be color coded and displayed on (overlapped with) the original B-mode ultrasound system. In a clinical application, such composite image can be used to identify fluid like (e.g., cysts) in soft tissues. Alternatively or in addition, the system of FIG. 24 can be configured to detect foreign bodies (e.g., metals, shrapnel) in tissue; and/or flaws in non-biological materials. In a related embodiment, the ultrasound imaging system portion of the overall system of FIG. 24 can be is replaced with alternative imaging modalities such as Magnetic Resonance (MR), for example, to measure the local displacement of the material under compression, from which the viscoelastic parameters can be deduced.

To effect the operation of an embodiment of the above-described system and implementation of the steps required to acquire and process the ultrasonic data representing results of the measurements of the sample(s) may require the operation of a processor controlled by application-specific instructions stored in a tangible memory element. Those skilled in the art should readily appreciate that required algorithmical functions, operations, and decisions may be implemented as computer program instructions, software, hardware, firmware or combinations thereof. Those skilled in the art should also readily appreciate that instructions or programs defining the functions and elements of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

Within this specification, embodiments have been described in a way that enables a clear and concise specification to be written, but it is intended and will be appreciated that embodiments may be variously combined or separated without parting from the scope of the invention. In particular, it will be appreciated that each of the features described herein is applicable to most if not all aspects of the invention.

In addition, when the present disclosure describes features of the invention with reference to corresponding drawings (in which like numbers represent the same or similar elements, wherever possible), the depicted structural elements are generally not to scale, for purposes of emphasis and understanding. It is to be understood that no single drawing is intended to support a complete description of all features of the invention. In other words, a given drawing is generally descriptive of only some, and not necessarily all, features of the invention. A given drawing and an associated portion of the disclosure containing a description referencing such drawing do not, generally, contain all elements of a particular view or all features that can be presented is this view, at least for purposes of simplifying the given drawing and discussion, and directing the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this particular detail in the drawing may be implied unless the context of the description requires otherwise. The described single features, structures, or characteristics of the invention may be combined in any suitable manner in one or more further embodiments.

The invention as recited in claims appended to this disclosure is intended to be assessed in light of the disclosure as a whole, including features disclosed in prior art to which reference is made.

For the purposes of this disclosure and the appended claims, the use of the terms "substantially", "approximately", "about" and similar terms in reference to a descriptor of a value, element, property or characteristic at hand is intended to emphasize that the value, element, property, or characteristic referred to, while not necessarily being exactly as stated, would nevertheless be considered, for practical purposes, as stated by a person of skill in the an. These terms, as applied to a specified characteristic or quality descriptor means "mostly", "mainly", "considerably". "by and large", "essentially", "to great or significant extent", "largely but not necessarily wholly the same" such as to reasonably denote language of approximation and describe the specified characteristic or descriptor so that its scope would be understood by a person of ordinary skill in the art. In one specific case, the terms "approximately", "substantially", and "about", when used in reference to a numerical value, represent a range of plus or minus 20% with respect to the specified value, more preferably plus or minus 10%, even more preferably plus or minus 5%, most preferably plus or minus 2% with respect to the specified value. As a non-limiting example, two values being "substantially equal" to one another implies that the difference between the two values may be within the range of +/−20% of the value itself, preferably within the +/−10% range of the value itself, more preferably within the range of +/−5% of the value itself, and even more preferably within the range of +/−2% or less of the value itself.

The use of these terms in describing a chosen characteristic or concept neither implies nor provides any basis for indefiniteness and for adding a numerical limitation to the specified characteristic or descriptor. As understood by a skilled artisan, the practical deviation of the exact value or characteristic of such value, element, or property from that stated falls and may vary within a numerical range defined by an experimental measurement error that is typical when using a measurement method accepted in the art for such purposes.

Modifications to, and variations of, the illustrated embodiments may be made without departing from the inventive concepts disclosed herein. Furthermore, disclosed aspects, or portions of these aspects, may be combined in ways not listed above. Accordingly, the invention should not be viewed as being limited to the disclosed embodiment(s). In addition, the terminology used herein is with the purpose of describing particular embodiments only, and is not intended to limit the scope of the present invention.

The invention claimed is:

1. A system for ultrasound imaging of a compressed target object, the system comprising:
   a compression device comprising a back plate, a pressure plate to interface with the target object, and one or more load sensors arranged between and coupling the back plate and the pressure plate, the device configured to apply a force to the target object, wherein the compression device is configured to vary an amount of force at a constant rate over a duration less than one second from an initial amount to a final predetermined amount, and, once the final predetermined amount is reached, to maintain said force at a substantially constant level;
   an ultrasound probe including an ultrasound transducer, said probe coupled to the back plate and configured to receive an ultrasound wave from the target object during a duration of time while the compression device holds the ultrasound probe in contact with the target object and while said force is being applied to the target object;
   an ultrasound imaging system cooperated with the ultrasound probe and configured to record a sequence of ultrasound image data frames during said duration of time, wherein the ultrasound image data frames represent a region of interest (ROI) of said target object;
   a compression device controller, operably cooperated with the compression device and including electronic circuitry programmed to set and control said constant rate and to synchronize an operation of the compression device with an operation of the ultrasound imaging system; and a data-processing unit configured to receive signal outputs produced at least by the ultrasound imaging system and the compression device controller to determine, based on said signal outputs, a value of local stress of the target object at each target object point that has been imaged, with the ultrasound imaging probe, as a function of time, wherein the pressure plate includes an opening that receives the ultrasound probe to allow contact between the ultrasound probe and the target object.

2. The system according to claim 1, configured to determine a value of loss angle parameter as a ratio of imaginary and real parts of a complex shear modulus of the target object that has been assessed independently from a distribution of the local stress in the target object, wherein the distribution of the local stress has been caused by the force applied to the target object with the use of the compression device.

3. The system according to claim 1, wherein the data-processing unit is further configured to perform at least one of the following:
  (i) to identify, based on said sequence of image frames and a signal output from the ultrasound imaging system, a target object location at which a time-dependence of said value of local stress does not follow a behavior of local stress expected in a viscoelastic medium, by (a) identifying a sign of a slope of said time-dependence, and (b) assigning a marker of unreliability to a portion of acquired data corresponding to a portion of the curve that has a negative sign;
  (ii) to form a map of loss angle parameter across an imaged portion of the target object and generate a data mask configured to eliminate data points associated with the marker of unreliability from said map;
  (iii) to filter out, from the signal outputs produced at least by the ultrasound imaging system and the compression device controller, an interference signal caused by presence of at least one of a cardiac pulsation, breathing motion, residual effect of initial ramping of the compression device, and noise, by processing said signal outputs within a frequency range that is devoid of such interference signal.

4. The system according to claim 1, wherein the ultrasound imaging system is configured to effectuate at least one of the following:
  (i) to display a map of the loss angle parameter as a color overlay over an image of the target object procured in B-mode of operation of the ultrasound probe;
  (ii) to record the sequence of the image frames, each image frame representing a 2D image of the target object;
  (iii) to record the sequence of the image frames each representing a 3D image of the target object and generate a signal output further used by the data-processing unit to determine the loss angle in 3D space; and
  (iv) to record the sequence of the image frames at a rate of hundreds of frames per second while the target object is insonated with an ultrasound wave shaped as either a substantially plane wave or a spatially-localized beam, wherein a shape of the ultrasound wave is chosen depending on a compression rate of the target object.

5. The system according to claim 1, wherein the data-processing unit is programmed to perform at least one of the following
  (i) to calculate a complex shear modulus at each ultrasonically-imaged point of the target object in frequency domain by directly converting values of local stress into Fourier domain; and
  (ii) to calculate a complex shear modulus at each ultrasonically-imaged point of the target object from a profile of values of the local stress in time domain; and
  once the complex shear modulus has been determined, calculate a loss angle parameter based on a ratio of imaginary and real parts of the complex shear modulus and form a map of said loss angle parameter across an imaged portion of the target object.

6. The system according to claim 2, wherein the data-processing unit is configured to determine the loss angle parameter in a range of frequencies defined to allow a determination of viscoelasticity of the target object as a function of at least one of frequency and time.

7. The system according to claim 6, wherein the data-processing unit is configured to determine the value of loss angle parameter based on determining the complex shear modulus of the target object in a sub-Hertz range of the range of frequencies.

8. The system according to claim 5, configured
  to accept a marking of a lesion area in at least one of the ultrasound image frames acquired with the ultrasound imaging system, said marking provided as an external input to the data-processing unit;
  to transfer said marking to the map of the loss angle parameter to identify said lesion area on the map; and
  to determine a first average value of the loss angle parameter within the lesion area of the map and a second average value of the loss angle parameter in a remaining portion of the map while not accounting for data at such points on the map at which a slope of time-dependence of said value of local stress has a negative sign.

9. A method for ultrasound imaging of a compressed target object, the method comprising:
  with an automated compression device comprising a back plate coupled to an ultrasound transducer, a pressure plate to directly contact a surface of the target object and having an opening that receives the ultrasound transducer such that the ultrasound transducer contacts the surface of the target object when the pressure plate directly contacts the surface of the target object, and at least one load sensor arranged between and coupling the back plate to the pressure plate, applying force to the target object while varying said force over a duration of less than one second from an initial value to the a final predetermined value and, once the final predetermined value is reached, maintaining said force at a substantially constant level;
  receiving an ultrasound wave from the target object, insonated with the ultrasound transducer during a period of time while the target object is compressed with said force;
  with an ultrasound imaging system, recording a sequence of ultrasound image data frames during said period, based on data from said ultrasound wave, wherein the ultrasound image data frames represent a region of interest (ROI) of said target object; and
  with a programmable computer processor, operably cooperated with at least the compression device and the ultrasound imaging system, determining a value of local stress at each target object point, that has been insonated with said ultrasound transducer, as a function of time.

10. The method according to claim 9, further comprising assessing a value of loss angle parameter as a ratio of imaginary and real parts of a complex shear modulus of the target object that has been assessed based on said data and independently from a distribution of the local stress in the target object.

11. The method according to claim 9, further comprising at least one of the following:
  (i) identifying, based on said sequence of image frames and a signal output from the ultrasound imaging system, a target object location at which a time-dependence of said value of local stress does not correspond to that in a viscoelastic medium, by (a) identifying a sign of a slope of said time-dependence, and (b) assigning a marker of unreliability to a portion of acquired data corresponding to a portion of the curve that has a negative sign;
  (ii) forming a map of loss angle parameter across an ultrasonically imaged portion of the target object and generating a data mask configured to eliminate data points associated with the marker of unreliability from said map;
  (iii) filtering out, from the signal outputs produced at least by the ultrasound imaging system and a controller of the compression device, an interference signal caused by presence of at least one of a cardiac pulsation, breathing motion, residual effect of initial ramping of the compression device, and noise, by processing said signal outputs within a frequency range that is devoid of such interference signal.

12. The method according to claim 9, further comprising at least one of the following:
  with a portion of the ultrasound imaging system, (i) displaying a map of the loss angle parameter as a color overlay over an image of the target object procured in B-mode of operation of the system;
  (ii) recording the sequence of the image frames, each image frame representing a 2D image of the target object;
  (iii) recording the sequence of the image frames each representing a 3D image of the target object and generate a signal output further used by a data-processing unit of the ultrasound imaging system to determine the loss angle in 3D space; and
  (iv) recording the sequence of the image frames at a rate of hundreds of frames per second while the target object is insonated with an ultrasound wave shaped as either a substantially plane wave or a spatially-localized beam, wherein a shape of the ultrasound wave is chosen depending on a compression rate of the target object with said force.

13. The method according to claim 9, further comprising at least one of the following
  (i) calculating a complex shear modulus at each ultrasonically-imaged point of the target object in frequency domain by directly converting values of local stress into Fourier domain; and
  (ii) calculating a complex shear modulus at each ultrasonically-imaged point of the target object from a profile of values of the local stress in time domain;
and further comprising:
  once the complex shear modulus has been determined, calculating a loss angle parameter based on a ratio of imaginary and real parts of the complex shear modulus and forming a map of said loss angle parameter across an imaged portion of the target object.

14. The method according to claim 10, further comprising assessing the loss angle parameter in a range of frequencies defined to allow a determination of viscoelasticity of the target object as a function of at least one of frequency and time.

15. The method according to claim 11, further comprising assessing the value of loss angle parameter based on the measurements of a complex shear modulus of the target object in a sub-Hertz frequency range.

16. The method according to claim 13, further comprising
  marking a lesion area in at least one of the ultrasound image frames, acquired with the ultrasound imaging system, said marking provided as an external input to the programmable computer processor of the system;
  transferring said marking to the map of the loss angle parameter to identify said lesion area on the map; and
  determining a first average value of the loss angle parameter within the lesion area of the map and a second average value of the loss angle parameter in a remaining portion of the map while not accounting for data at such points on the map at which a slope of time-dependence of said value of local stress has a negative sign.

17. A method for ultrasound imaging of a compressed target object, the method comprising:
  with an automated compression device, applying force to the target object while varying said force over a duration of less than one second from an initial value to the a final predetermined value and, once the final predetermined value is reached, maintaining said force at a substantially constant level;
  receiving an ultrasound wave from the target object, insonated with an ultrasound transducer of an ultrasound probe during a period of time while the target object is compressed with said force;
  with an ultrasound imaging system, recording a sequence of ultrasound image data frames during said period, based on data from said ultrasound wave, wherein the ultrasound image data frames represent a region of interest (ROI) of said target object;
  with a programmable computer processor operably cooperated with at least the compression device and the ultrasound imaging system, determining a value of local stress at each target object point, that has been insonated with said ultrasound transducer, as a function of time;
  calculating a complex shear modulus at each ultrasonically-imaged point of the target object by at least one of:
    (i) in frequency domain by directly converting values of local stress into Fourier domain;
    (ii) from a profile of values of the local stress in time domain;
  once the complex shear modulus has been determined, calculating a loss angle parameter based on a ratio of imaginary and real parts of the complex shear modulus and forming a map of said loss angle parameter across an imaged portion of the target object;
  marking a lesion area in at least one of the ultrasound image frames, acquired with the ultrasound imaging system, said marking provided as an external input to the programmable computer processor of the system;

transferring said marking to the map of the loss angle parameter to identify said lesion area on the map; and determining a first average value of the loss angle parameter within the lesion area of the map and a second average value of the loss angle parameter in a remaining portion of the map while not accounting for data at such points on the map at which a slope of time-dependence of said value of local stress has a negative sign.

* * * * *